United States Patent
Ishida

(10) Patent No.: US 10,238,840 B2
(45) Date of Patent: Mar. 26, 2019

(54) CATHETER ASSEMBLY

(71) Applicant: TERUMO KABUSHIKI KAISHA, Tokyo (JP)

(72) Inventor: Masahiro Ishida, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 89 days.

(21) Appl. No.: 15/294,137

(22) Filed: Oct. 14, 2016

(65) Prior Publication Data

US 2017/0028171 A1     Feb. 2, 2017

Related U.S. Application Data

(63) Continuation of application No. PCT/JP2016/063913, filed on May 10, 2016.

(30) Foreign Application Priority Data

May 15, 2015     (JP) .................................. 2015-100353

(51) Int. Cl.
    *A61M 25/06*     (2006.01)
    *A61M 25/00*     (2006.01)
    *A61M 25/01*     (2006.01)

(52) U.S. Cl.
    CPC .... *A61M 25/0606* (2013.01); *A61M 25/0017* (2013.01); *A61M 25/0618* (2013.01); *A61M 25/0668* (2013.01); *A61M 25/0113* (2013.01)

(58) Field of Classification Search
    CPC .... A61M 2025/028; A61M 2005/1586; A61M 5/158; A61M 25/0612; A61M 25/06; A61M 25/0113
    See application file for complete search history.

(56) References Cited

U.S. PATENT DOCUMENTS

| | | | | |
|---|---|---|---|---|
| 5,312,369 A | * | 5/1994 | Arcusin | A61M 5/3216 |
| | | | | 604/192 |
| 6,997,912 B1 | * | 2/2006 | Tristan | A61M 5/158 |
| | | | | 604/192 |
| 2013/0023826 A1 | * | 1/2013 | Ishida | A61M 5/158 |
| | | | | 604/165.02 |

FOREIGN PATENT DOCUMENTS

| | | |
|---|---|---|
| JP | 2013-529111 A | 7/2013 |
| WO | WO-2011/143621 A1 | 11/2011 |

* cited by examiner

*Primary Examiner* — Deanna K Hall
(74) *Attorney, Agent, or Firm* — Foley & Lardner LLP

(57) ABSTRACT

A catheter assembly includes a hollow catheter; a catheter hub configured to fix and hold the catheter; an inner needle including a needle tip and configured to be removably inserted through an inside of the catheter; a needle hub configured to fix and hold the inner needle; and a catheter operation member capable of moving the catheter relative to the inner needle. The catheter operation member includes a holding portion configured to directly hold the catheter in a detachable manner.

20 Claims, 13 Drawing Sheets

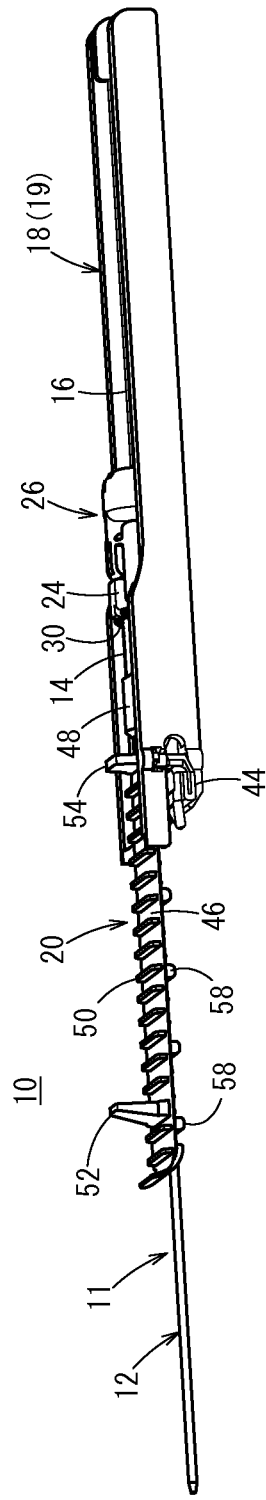
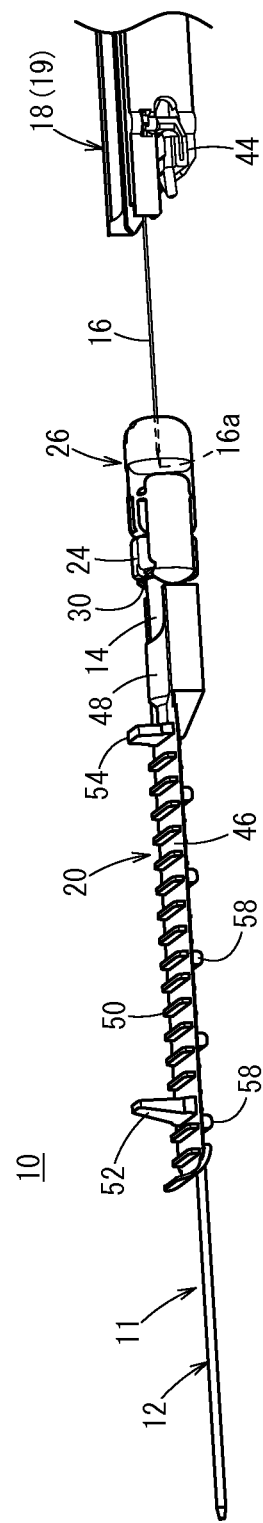

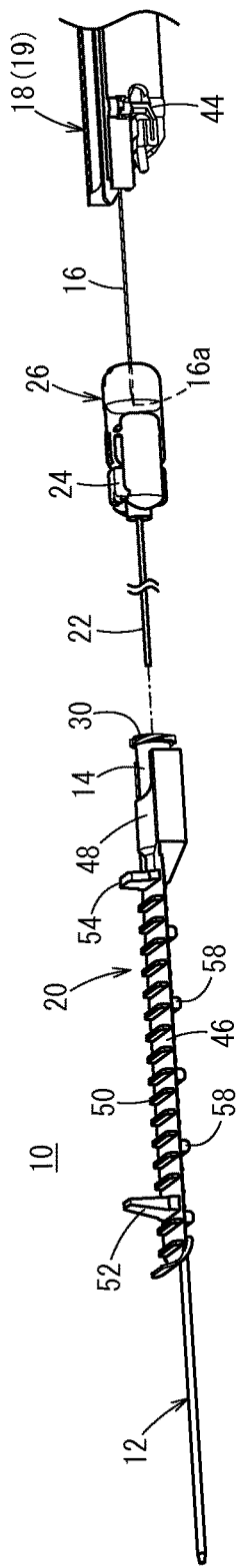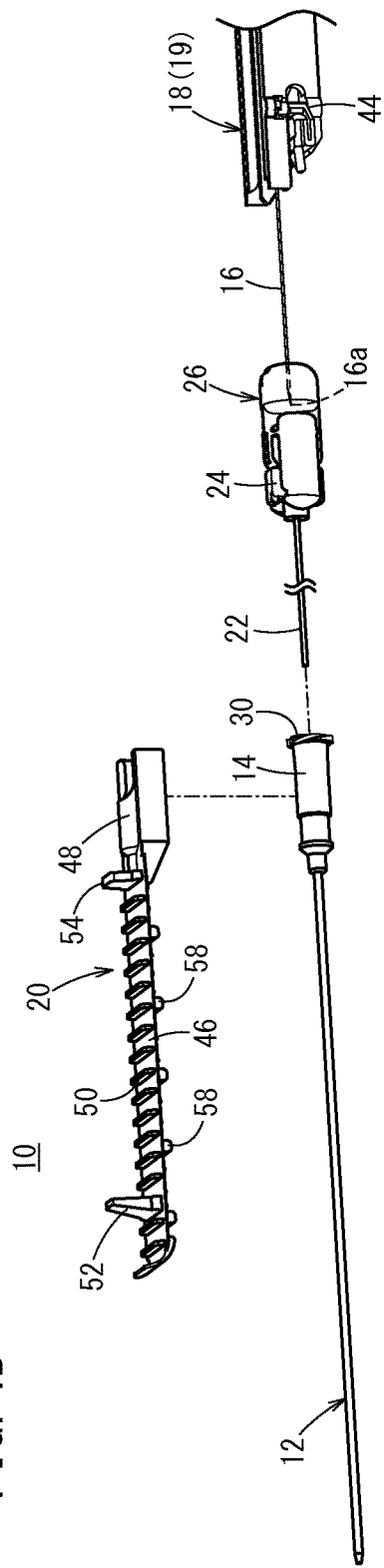

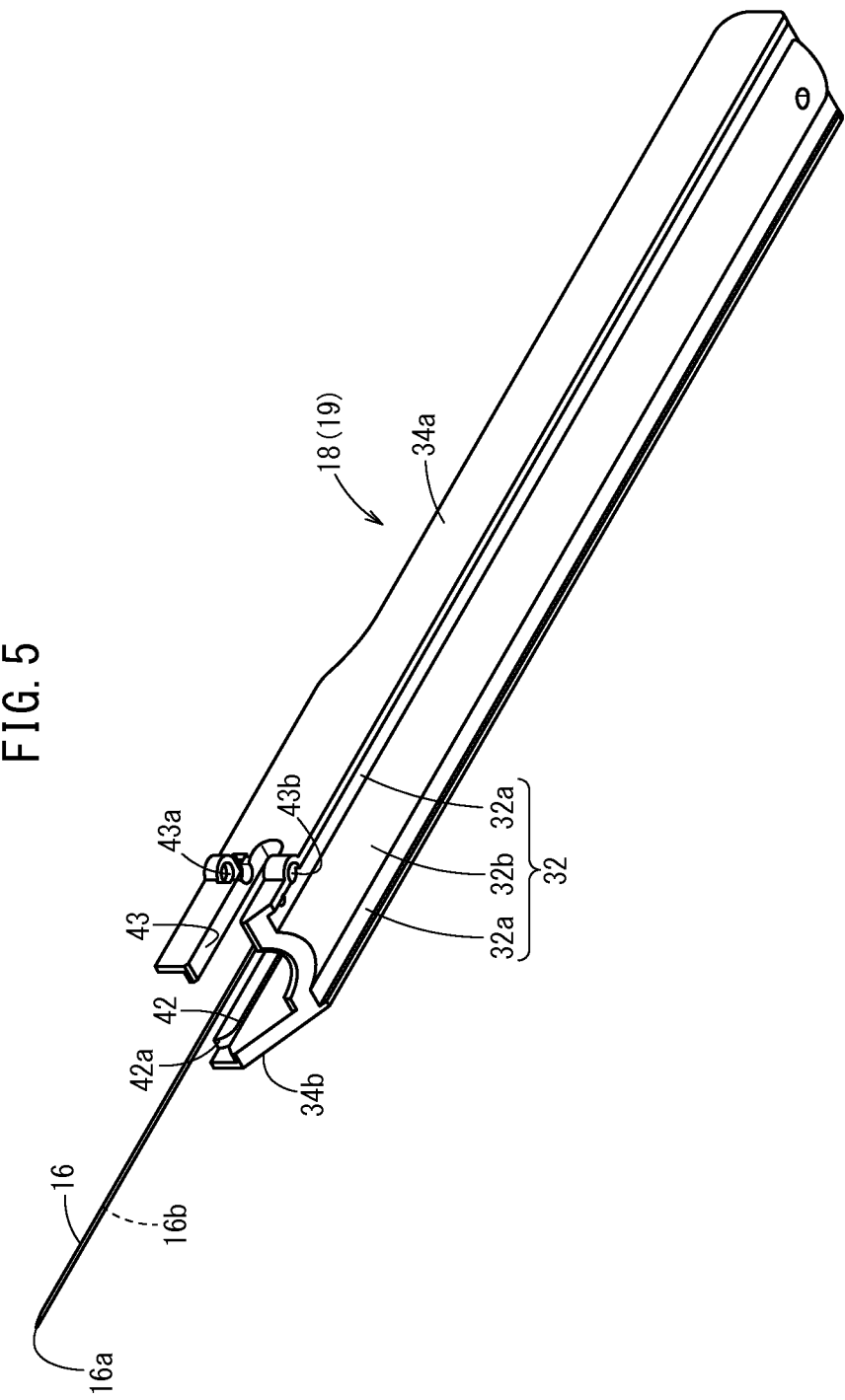

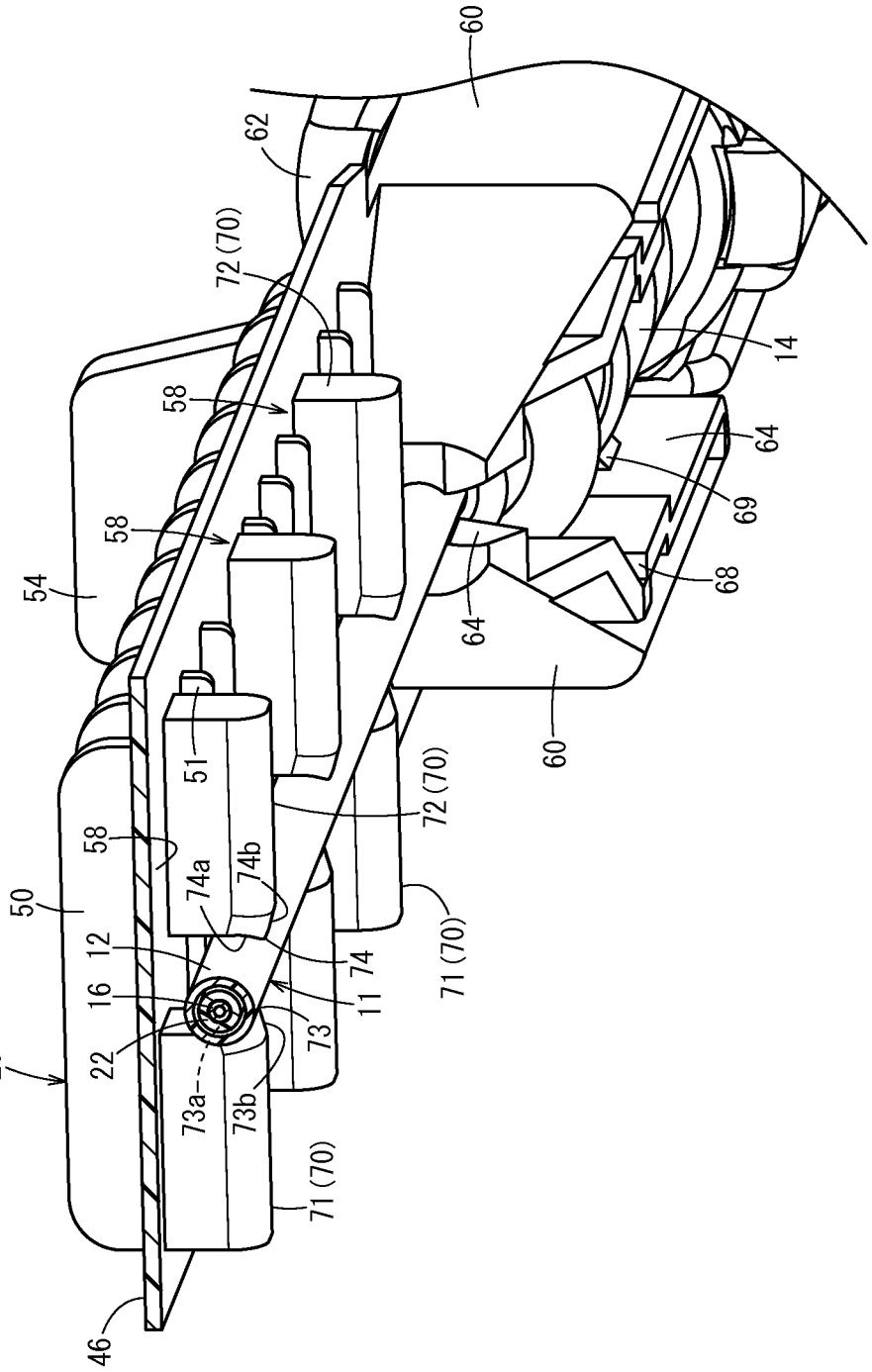

CATHETER ASSEMBLY

CROSS-REFERENCE TO RELATED APPLICATIONS

The present application is a continuation of PCT Application No. PCT/JP2016/063913, filed on May 10, 2016, which claims priority to Japanese Patent Application No. 2015-100353, filed on May 15, 2015, both of which are hereby incorporated by reference in their entireties.

BACKGROUND

Technical Field

The present disclosure relates to a catheter assembly adapted to puncture a blood vessel and be indwelled while performing infusion to a patient, for example.

Background Art

In the related art, a catheter assembly is used while performing infusion to a patient. This kind of the catheter assembly includes a hollow catheter, a catheter hub fixed to a proximal end of the catheter, a hollow inner needle inserted into the catheter and having a sharp needle tip at a distal end, and a needle hub fixed to a proximal end of the inner needle (refer to JP 2013-529111 A).

Furthermore, in the catheter assembly disclosed in JP 2013-529111 A, because the catheter is inserted deep into the patient's body, the long catheter and the inner needle are housed in a manner stacking in two layers and extending in an axial direction inside the cylindrical-shaped needle hub. A user, such as a doctor or a nurse, punctures the patient with the catheter and the inner needle, and advances a catheter operation member connected to the catheter hub in this puncturing state, thereby making the catheter advance relative to the inner needle and inserting the catheter into the body.

SUMMARY

In the above-described type of catheter assembly, a catheter extending inside a needle hub is arranged in a manner not contacting the needle hub in order to secure smooth mobility of the catheter. In other words, a space is formed between an outer peripheral surface of the catheter and an inner surface of the needle hub. However, in the case where such a space exists, the catheter or the inner needle may be warped inside the needle hub by reaction force received from a patient at the time of puncturing the patient with the long catheter and an inner needle, and a user may feel difficulty in puncturing.

Certain embodiments of the present invention can help to solve the above-described problem and are directed to providing a catheter assembly in which a catheter and an inner needle can be prevented from being warped along with puncture while mobility of the catheter is secured, and a user can smoothly perform operation without feeling any discomfort.

To achieve the above-described object, a catheter assembly according to one embodiment of the present invention includes: a hollow catheter; a catheter hub adapted to fix and hold the catheter; an inner needle including a needle tip and adapted to be removably inserted through inside of the catheter; a needle hub adapted to fix and hold the inner needle; and a catheter operation member capable of moving the catheter relative the inner needle, and the catheter assembly is characterized in that the catheter operation member includes a holding portion adapted to directly hold the catheter in a detachable manner.

According to above, in the catheter assembly, the holding portion of the catheter operation member directly holds the catheter in a freely detachable manner. Therefore, the catheter and the inner needle can be prevented from being warped while mobility of the catheter is secured. More specifically, the catheter operation member properly maintains an extending state of the catheter by directly holding the catheter inside the needle hub, and prevents the catheter from being warped even in the case of receiving resistance force at the time of puncture with the catheter ad the inner needle. Therefore, a user can properly puncture the patient with the catheter and the inner needle, which are prevented from being warped, without feeling any discomfort. Furthermore, the catheter operation member can make the catheter being held smoothly advance and retract relative to the inner needle and the needle hub.

Preferably, the catheter operation member extends in a longitudinal direction of the needle hub and includes an elongated portion provided with the holding portion, and the elongated portion can be curved in a direction separating away from the inner needle.

Thus, because the elongated portion can be curved in the direction separating away from the inner needle, the catheter operation member is curved when the user performs an advancing operation, and inconvenience, such as interference with the patient and difficulty with advancement, is avoided. Furthermore, the catheter operation member can easily perform holding and holding release of the catheter with the holding portion based on a change between a curved state and a non-curved state of the elongated portion.

In addition to the above-described configuration, the elongated portion may be engaged with the needle hub in a manner relatively movable, and the needle hub may inhibit the elongated portion from being curved in a state that the elongated portion is engaged with the needle hub.

Thus, because the elongated portion is inhibited from being curved in the state of being engaged with the needle hub, advancing and retracting can be smoothly performed inside the needle hub and also the catheter can be stably held by the holding portion.

Furthermore, the catheter may be detached from the holding portion against engagement force of the holding portion by curving the elongated portion in a direction separating away from the inner needle.

Thus, the catheter operation member can easily perform holding release of the catheter by detaching the catheter against engagement force of the holding portion due to curving of the elongated portion.

Furthermore, preferably, the elongated portion holds the catheter with the holding portion by being housed in the needle hub in a manner formed in a linear shape in a width direction in front sectional view Thus, because the elongated portion holds the catheter in a manner formed in the linear shape in the width direction, the elongated portion is prevented from being warped, twisted, dropped, and the like inside the needle hub, and the catheter can be more stably held by the holding portion.

Alternatively, the catheter may be automatically detached from the holding portion by curving the elongated portion in a direction separating away from the inner needle.

Thus, because the elongated portion automatically detaches the catheter from the holding portion, holding release of the catheter can be smoothly performed based on change from the curved state to the non-curved state.

Furthermore, preferably, the elongated portion holds the catheter with the holding portion by being housed in the needle hub in a manner formed in a bent shape in a width direction in a front sectional view, and the catheter is released from being held with the holding portion by forming the elongated portion in a linear shape in a width direction as the elongated portion is curved in a direction separating away from the inner needle.

Thus, because the elongated portion surely is housed in the needle hub in a manner formed in the bent shape in the width direction, the catheter can be more surely held with the holding portion. On the other hand, because the elongated portion is deformed so as to be formed in the linear shape in the width direction along with exposure from the needle hub, the catheter can be easily detached from the holding portion.

Additionally, preferably, a bendable portion adapted to induce the elongated portion to be formed in the bent shape in the width direction in a front sectional view is provided in a center portion in the width direction of the elongated portion.

Thus, because the elongated portion includes the bendable portion, the bent shape having a top at the center portion in the width direction of the elongated portion can be easily formed, and the catheter can be stably held by the holding portion.

Here, preferably, a plurality of the holding portions is provided in an axial direction of the catheter.

Thus, because the plurality of holding portions is provided in the axial direction of the catheter, the catheter operation member can firmly hold the entire catheter even though holding force of each holding portion is weak. Additionally, the catheter operation member can release holding of the catheter from the holding portions sequentially from a distal end side, and insertion of the catheter can be smoothly continued because the holding portion on a proximal end side holds the catheter even in the case of receiving reaction force at the time of inserting the catheter.

In this case, the holding portion may also be formed in a manner gradually becoming larger in a proximal end direction of the catheter operation member.

Thus, because the plurality of holding portions is formed in a manner gradually becoming larger in the proximal end direction, the holding portion on the proximal end side can properly hold the catheter in the vicinity of a connecting portion between the catheter and the catheter hub. Therefore, assembly of the catheter and the catheter operation member can be simplified.

Furthermore, preferably, the holding portion includes a pair of projecting portions adapted to nip the catheter.

The pair of projecting portions can contact and hold an outer peripheral surface of the catheter with suitable engagement force by inserting the catheter between these projecting portions.

Additionally, preferably, the projecting portions of each pair of projecting portion are offset from one another in an axial direction of the catheter.

Thus, because the projecting portions of each pair of projecting portion are offset from one another in an axial direction of the catheter, engagement force of the pair of projecting portions with respect to the catheter can be easily released, and impact and the like on the catheter can be suppressed at the time of holding release.

Furthermore, preferably, the pair of projecting portions includes nail portions projecting in directions toward each other and adapted to hook and hold the catheter, and taper portions inclined inward in a width direction and toward a holding section are provided on an opposite side of the holding section for the catheter in the nail portions.

Thus, because the pair of projecting portions includes the taper portions, the taper portions can easily guide the catheter to the holding section for the catheter in the nail portions. With this structure, at the time of making the catheter operation member retract, the catheter detached at the time of advancing is guided to the holding portion, and a holding state of the catheter with the holding portion can be easily restored.

Moreover, preferably, the catheter operation member includes a hub attachment portion attached to the catheter hub and adapted to transmit operation force of a user to the catheter hub.

Thus, because the catheter operation member not only holds the catheter but also holds the catheter hub with the hub attachment portion, the operation force applied to the catheter operation member from the user can be more surely transmitted to the catheter and the catheter hub.

Furthermore, preferably, the needle hub includes a guide portion adapted to guide the catheter operation member in a direction separating away from the inner needle at the time of moving the catheter operation member in the distal end direction.

Thus, because the needle hub includes the guide portion, when a user performs advancing operation of the catheter operation member in the distal end direction, the user can detach the catheter operation member from the inner needle and smoothly separate the catheter while making the catheter advance.

According to certain embodiments of the present invention, the catheter assembly can prevent the catheter and the inner needle from being warped along with puncture while securing mobility of the catheter, and the user can smoothly perform operation without feeling any discomfort.

BRIEF DESCRIPTION OF THE DRAWINGS

FIG. 3A is a first explanatory diagram illustrating operation at the time of using the catheter assembly, and FIG. 3B is a second explanatory diagram illustrating operation of the catheter assembly subsequent to FIG. 3A.

FIG. 4A is a third explanatory diagram illustrating operation of the catheter assembly subsequent to FIG. 3B, and FIG. 4B is a fourth explanatory diagram illustrating operation of the catheter assembly subsequent to FIG. 4A.

FIG. 5 is a perspective view of an inner needle and a housing when viewed from an angle different from FIG. 2.

FIG. 7 is a cross-sectional perspective view taken along a line VII-VII in FIG. 6.

DETAILED DESCRIPTION

In the following description, catheter assemblies according to embodiments of the present invention will be described in detail with reference to the attached drawings.

In the case of performing transfusion, blood transfusion, and the like to a patient (living body), a catheter assembly 10 according to an embodiment of the present invention is used to construct an introducing portion for medicinal solution and the like by being tapped into the patient's body and indwelled. The catheter assembly 10 may be formed longer than a peripheral venous catheter (such as a central intravenous catheter, a PICC, and a midline intravenous catheter). Alternatively, the catheter assembly 10 may be formed as a peripheral venous catheter. Furthermore, the catheter assembly 10 is not limited to a venous catheter and may also be formed as an artery catheter such as peripheral artery catheter.

First Embodiment

Figure 1:
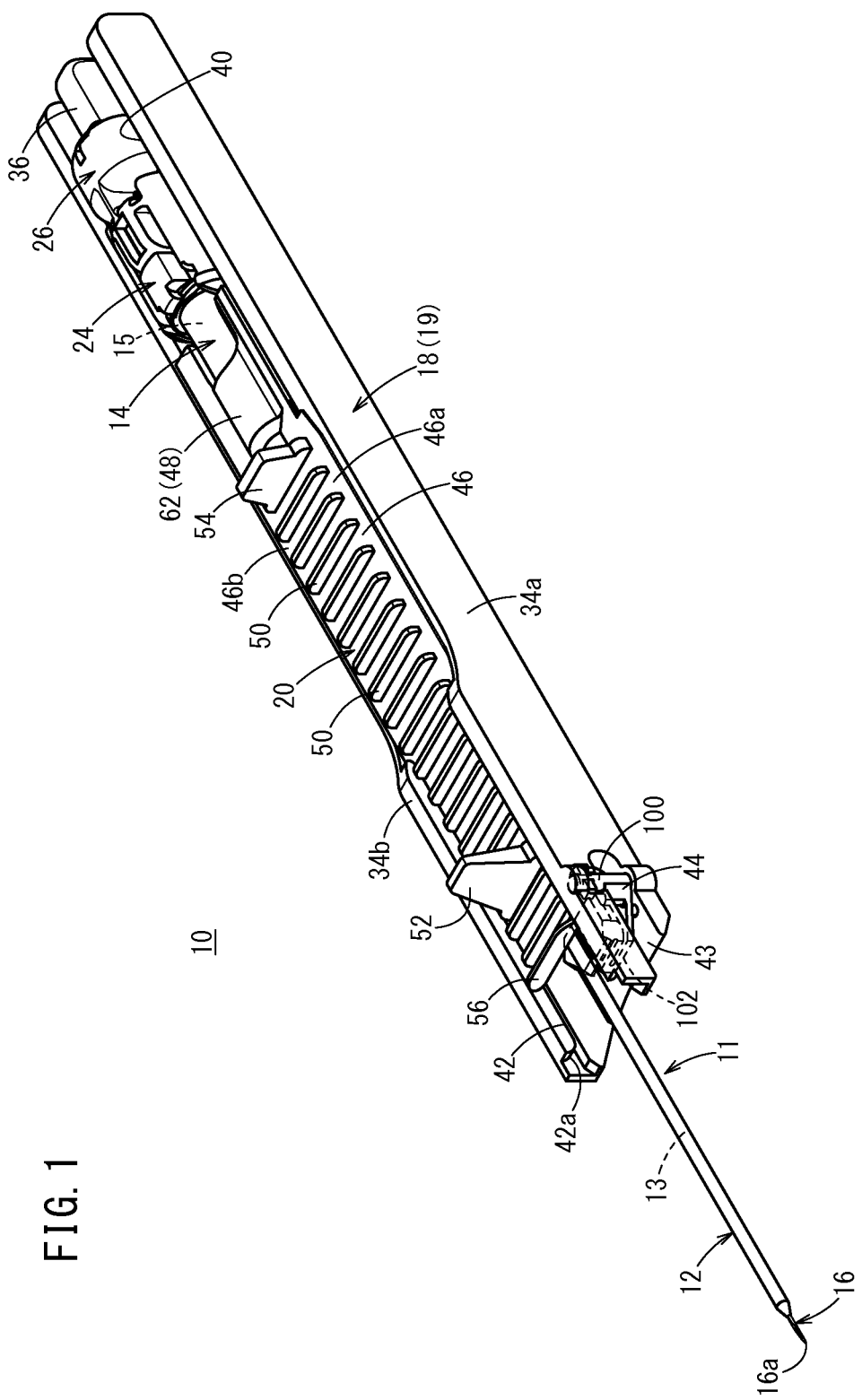
FIG. 1 is a perspective view illustrating an entire structure of a catheter assembly according to a first embodiment of the present invention.
Figure 2:
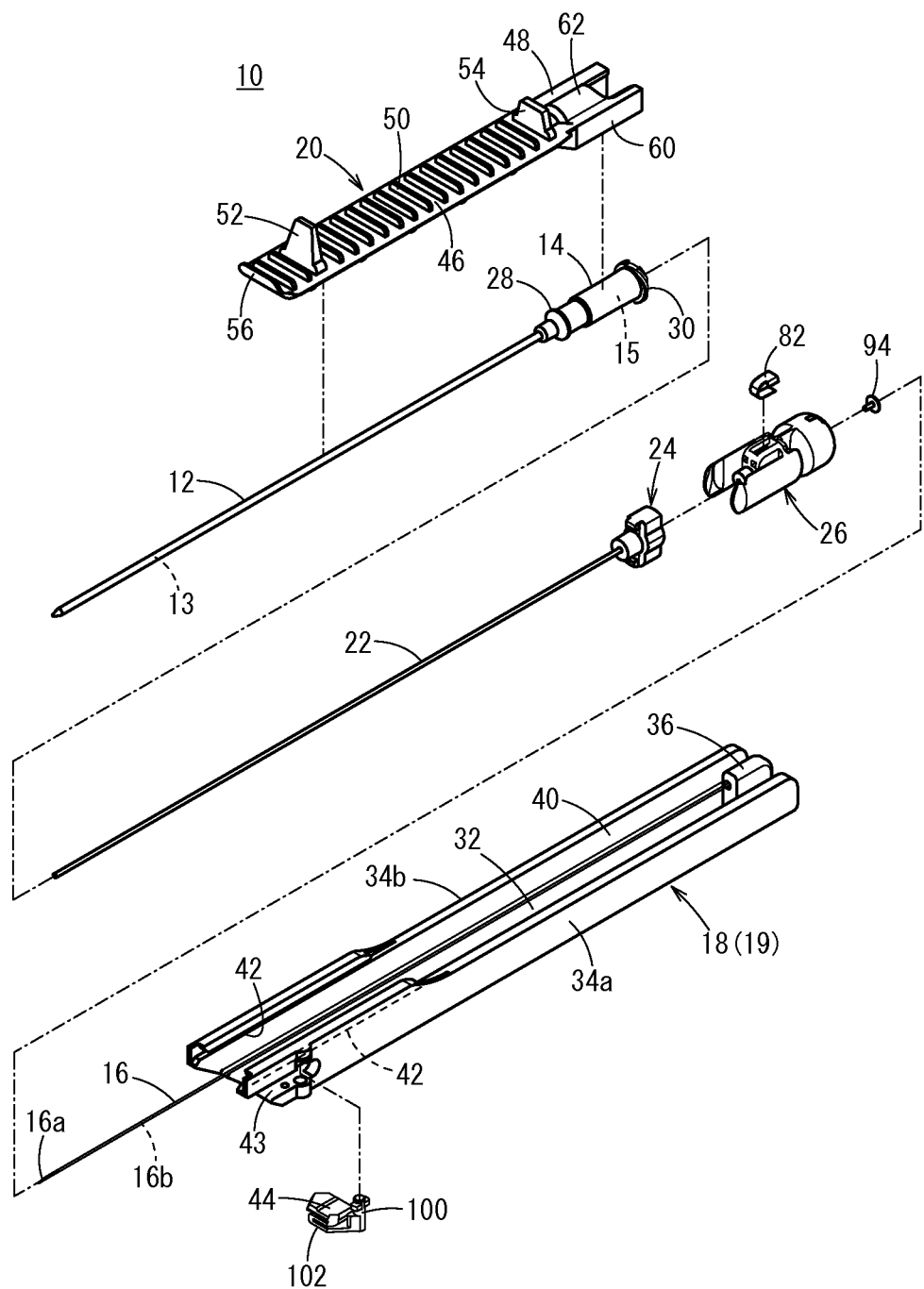
FIG. 2 is an exploded perspective view illustrating the catheter assembly in FIG. 1.

As illustrated in FIGS. 1 and 2, a catheter assembly 10 according to a first embodiment includes a catheter 12, a catheter hub 14 to fix and hold the catheter 12, a hollow inner needle 16 inserted into the catheter 12, a needle hub 18 to fix and hold the inner needle 16, a catheter operation member 20 attached to an upper side of the catheter hub 14, a tube-like auxiliary member 22 inserted between the catheter 12 and the inner needle 16, an auxiliary member hub 24 to fix and hold the auxiliary member 22, and a needle protection member 26 connected to the catheter hub 14 and a proximal end of the auxiliary member hub 24.

In an initial state before use, the catheter assembly 10 has a multiple tube structure (multiple tube unit 11) in which the catheter 12, auxiliary member 22, and inner needle 16 are stacked sequentially from the outside. The catheter operation member 20 has a structure to directly hold the multiple tube unit 11. Additionally, in the initial state, the catheter assembly 10 houses, inside the needle hub 18, part of the multiple tube unit 11, catheter hub 14, catheter operation member 20, auxiliary member 24, and needle protection member 26 by suitably assembling these components.

A user such as a doctor or a nurse grips the needle hub 18 of the catheter assembly 10 in the initial state illustrated in FIG. 1 and punctures a blood vessel (venous or artery) of the patient with a distal end of the multiple tube unit 11. The user performs advancing operation of the catheter operation member 20 relative to the needle hub 18 while keeping the puncturing state, thereby making the catheter 12 advance more to a distal end side (deeper inside the blood vessel) than the inner needle 16.

The catheter assembly 10 integrally moves the catheter hub 14 connected to the catheter operation member 20, auxiliary member hub 24, and needle protection member 26 as illustrated in FIG. 3A along with advancement of the catheter 12 or retraction of the needle hub 18 relative to the catheter 12. At this point, because the inner needle 16 is fixed to the needle hub 18, the multiple tube unit 11 is shifted to have a double-stack structure of the catheter 12 and the auxiliary member 22. Furthermore, the catheter operation member 20 releases the multiple tube unit 11 from being held at the time of performing advancing operation of the catheter 12.

In the case of continuing advancement, a portion up to the needle protection member 26 slips out from the distal end of the needle hub 18, and a needle tip 16a of the inner needle 16 is housed inside the needle protection member 26 as illustrated in FIG. 3B. Then, as illustrated in FIG. 4A, the catheter 12 and the catheter hub 14 become separable from the auxiliary member hub 24 and the needle protection member 26 which have slipped out from the needle hub 18, and are detached from the auxiliary member 22 along with continuous advancement. Finally, as illustrated in FIG. 4B, the catheter 12 and the catheter hub 14 are indwelled in the patient by detachment of the catheter operation member 20 from the catheter hub 14. In the following, a structure of the catheter assembly 10 will be specifically described.

As illustrated in FIG. 2, the catheter 12 of the catheter assembly 10 has flexibility, and a cavity 13 is formed inside in a penetrating manner. The cavity 13 is formed to have a diameter in which the inner needle 16 and the auxiliary member 22 can be housed and medicinal solution, blood, and the like can flow. A length of the catheter 12 is not particularly limited and can be suitably designed in accordance with usage, conditions, and the like, and for example, the length is set to about 14 to 500 mm, set to about 30 to 400 mm, or set to about 76 to 200 mm.

A constituent material of the catheter 12 is not limited, but a soft resin material may be suitable, and for example, fluororesins such as polytetrafluoroethylene (PTFE), ethylene-tetrafluoroethylene copolymer (ETFE), perfluoroalkoxy fluororesin (PFA), olefin resins such as polyethylene and polypropylene, or mixtures thereof, polyurethane, polyesters, polyamides, polyether nylon resins, and mixtures of the olefin resin and ethylene/vinyl acetate copolymer, and the like may be exemplified.

A proximal end of the catheter 12 is fixed to a distal end of the catheter hub 14 by a suitable fixing method (caulking, fusion, bonding, and the like). The catheter hub 14 is exposed on patient's skin in a state that the catheter 12 is inserted into a blood vessel, and indwelled together with the catheter 12 by being pasted with a tape or the like.

The catheter hub 14 is formed in a cylindrical shape tapered in a distal end direction. A constituent material of the catheter hub 14 is not particularly limited, but for example, thermoplastic resins such as polypropylene, polycarbonate, polyamides, polysulfone, polyarylate, and methacrylate-butylene-styrene copolymer may be applied. A transfusion tube connector not illustrated is connected to a proximal end side of the catheter hub 14 after detachment of the inner needle 16.

A hollow portion 15 that is in communication with the cavity 13 of the catheter 12 and allows transfusion solution to flow is provided inside the catheter hub 14. The hollow portion 15 may house a hemostasis valve, a plug, and the like not illustrated adapted to prevent back-flow of blood at the time of puncture with the inner needle 16 and also enable transfusion along with insertion of the transfusion tube connector.

Furthermore, an annular projection 28 which projects radially outward and revolves in a circumferential direction of the catheter hub 14 is formed close to a distal end of an outer peripheral surface of the catheter hub 14. Additionally, same as the annular projection 28, a screw portion 30 that revolves in the circumferential direction of the catheter hub 14 is formed in a projecting manner at a proximal end of the outer peripheral surface of the catheter hub 14.

On the other hand, the inner needle 16 of the catheter assembly 10 is formed as a hollow tube having rigidity capable of puncturing skin of a living body, and arranged in the cavity 13 of the catheter 12 and the hollow portion 15 of the catheter hub 14 in a penetrating manner. The inner needle 16 has an entire length longer than the catheter 12 and is formed so as to have a diameter gradually becoming larger in the distal end direction from the proximal end portion, and the distal end thereof is provided with a sharp needle tip 16a. In the initial state illustrated in FIG. 1, the multiple tube unit 11 exposes the needle tip 16a from the catheter 12 and the auxiliary member 22. A through-hole 16b is provided inside the inner needle 16 in an axial direction of the inner needle 16. Meanwhile, a groove portion (not illustrated) may also be provided in the axial direction on an outer peripheral surface of the inner needle 16. Additionally, the inner needle 16 may also be a solid needle.

As a constituent material of the inner needle 16, for example, metallic materials such as stainless steel, aluminum or an aluminum alloy, or titanium or a titanium alloy, a hard resin, ceramics, and the like may be exemplified. The inner needle 16 is firmly fixed to the needle hub 18 by a suitable fixing method (fusion, bonding, insert molding, and the like).

As illustrated in FIG. 5, the needle hub 18 is formed as a housing 19 including a lower wall 32, a pair of side walls 34a, 34b projecting upward from a side portions 32a of the lower wall 32. The housing 19 has an elongated cup-like shape extending shorter than an axial length of the inner needle 16. A housing space 40 to house part of the multiple tube unit 11, the catheter hub 14, auxiliary member hub 24, and needle protection member 26 is formed on an inner side surrounded by the lower wall 32 and the pair of side walls 34a, 34b.

A constituent material to form the needle hub 18 is not particularly limited and, for example, may be suitably selected from materials exemplified for the catheter hub 14. Meanwhile, in the catheter assembly 10, the catheter hub 14 and the needle protection member 26 are exposed on the upper side in order to enable rotation of the catheter 12 relative to the inner needle 16. Alternatively, the catheter assembly 10 may also have a structure in which the catheter hub 14 and the needle protection member 26 are covered by forming an upper wall or attaching a lid body on the housing 19.

The lower wall 32 includes: a pair of the side portions 32a formed flat; and a guide groove portion 32b interposed between the pair of the side portions 32a and recessed downward in an arc shape. In the guide groove portion 32b, the catheter hub 14, auxiliary member hub 24, and needle protection member 26 are slidably arranged in a longitudinal direction of the housing 19. A needle holding portion 36 is integrally formed on a proximal end side and in a center portion in a width direction (guide groove portion 32b) of the lower wall 32. The needle holding portion 36 projects upward from an upper surface of the lower wall and fixes the proximal end portion of the inner needle 16 at a predetermined height. Meanwhile, the needle holding portion 36 may also be formed separately from the housing 19 and may be bonded and fixed to the housing 19.

The pair of side walls 34a, 34b extends in parallel in a longitudinal direction together with the lower wall 32 and have a constant vertical width on the proximal end side and an intermediate side, and the vertical width on the distal end side is formed wider relative to the intermediate side. A groove-like rail portion 42 is provided on an upper portion on the distal end side of each of the side walls 34a, 34b. The pair of rail portions 42 linearly extends in the longitudinal direction on an inner surface of the wide portion in each of the side walls 34a, 34b, and reaches an upper surface on the intermediate side. The respective rail portions 42 house side edges 46a, 46b of the catheter operation member 20, and guide the catheter operation member 20 to advance and retract. A distal end of a groove wall constituting the rail portion 42 is formed to have a curved surface 42a to allow the catheter operation member 20 to be curved.

Furthermore, an arrangement recessed portion 43 to attach a support member 44 is provided on the side wall 34a. The arrangement recessed portion 43 is cut out in the proximal end direction from the distal end of the side wall 34a, and located between the lower wall 32 and the rail portion 42. The lower wall 32 and the side wall 34a at a forming position of the arrangement recessed portion 43 are provided with a pair of bearing holes 43a, 43b to rotatably attach the support member 44.

Referring back to FIG. 2, the auxiliary member 22 of the catheter assembly 10 supports the catheter 12 from the inside and has a function to assist insertion of the catheter 12 into a blood vessel. The auxiliary member 22 has an outer diameter smaller than an inner diameter of the catheter 12, and is formed in a hollow tube having an inner diameter larger than an outer diameter of the inner needle 16. A proximal end portion of the auxiliary member 22 is fixed to and held by the auxiliary member hub 24 by a suitable fixing method (caulking, fusion, bonding, and the like).

The auxiliary member hub 24 has a distal end side thereof assembled to the catheter hub 14 in a freely detachable manner, and the needle protection member 26 is assembled to a proximal end side thereof in a freely detachable manner. The auxiliary member hub 24 connects the catheter hub 14 and the needle protection member 26 respectively in a manner integrally rotatable. Meanwhile, the auxiliary member hub 24 may also integrated to the needle protection member 26 (more specifically, the auxiliary member 22 may also be fixed to the needle protection member 26). Furthermore, the catheter assembly 10 may not necessarily include the auxiliary member 22 and the auxiliary member hub 24. In this case, the needle protection member 26 is directly attached to the proximal end of the catheter hub 14.

In the initial state, the needle protection member 26 has the inner needle 16 arranged in a penetrating manner. Furthermore, the needle tip 16a having moved along with detachment of the catheter 12 and the inner needle 16 is housed, and the needle tip 16a is prevented from being exposed again. The needle protection member 26 houses a shutter 82 and a slip-out stop member 94 inside thereof in order to prevent the needle tip 16a from being exposed again. The shutter 82 is elastically deformed by contacting the outer peripheral surface of the inner needle 16 in a state that the inner needle 16 is arranged in a penetrating manner, and the shutter 82 is elastically restored and shuts a penetrating route of the inner needle 16 when the needle tip 16a slips out. The slip-out stop member 94 includes a hole having a diameter smaller than that of the needle tip 16a of the inner needle 16, thereby inhibiting the needle tip 16a from slipping out in the proximal end direction.

Figure 6:
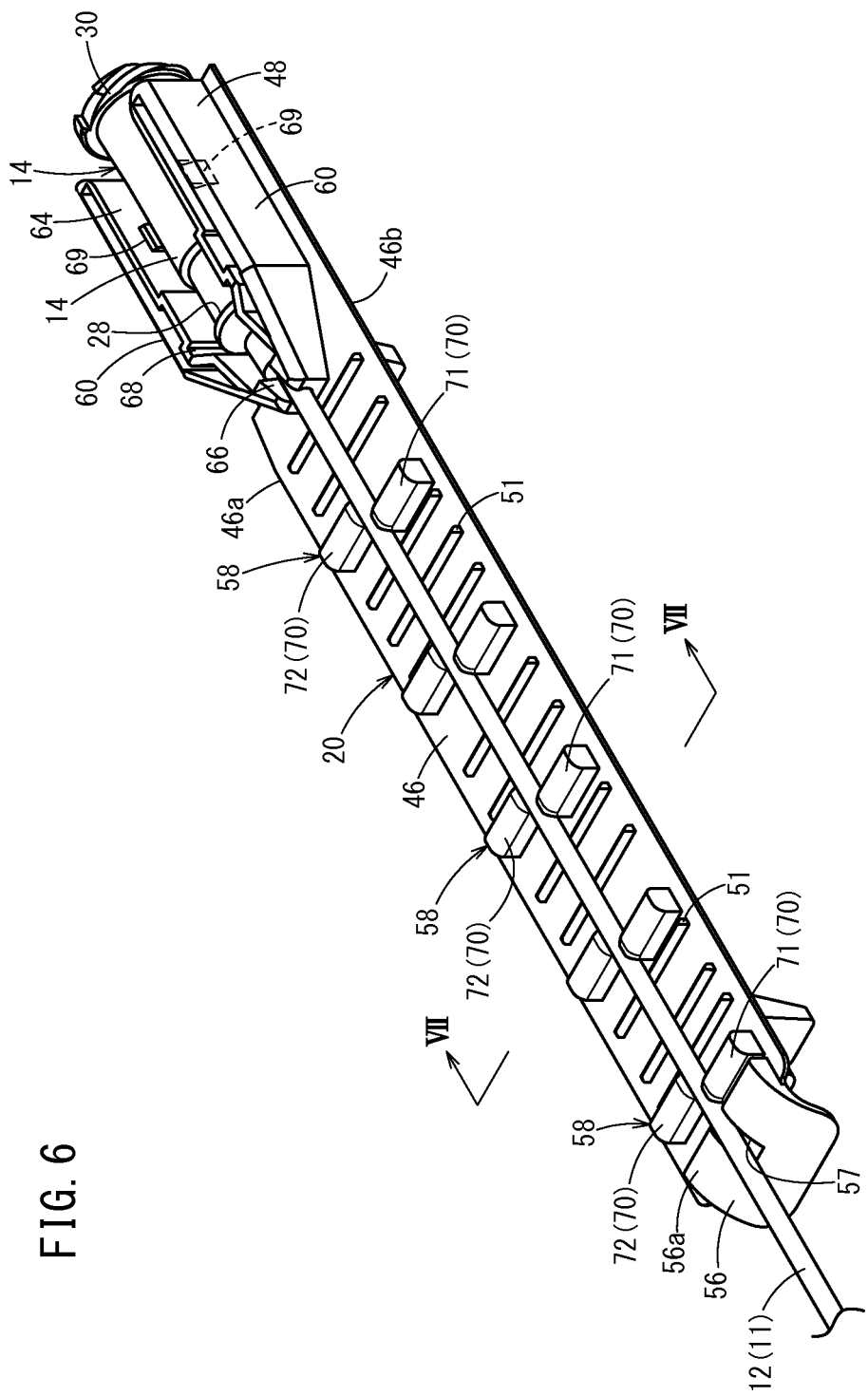
FIG. 6 is a perspective view of a catheter operation member when viewed from an angle different from FIG. 2.

The catheter operation member 20 directly holds the catheter 12 and also is attached to the catheter hub 14, thereby making the catheter 12 and the catheter hub 14 advance and retract relative to the inner needle 16 and the housing 19. As illustrated in FIGS. 2 and 6, the catheter operation member 20 includes an operation plate portion 46 (elongated portion) extending in the longitudinal direction of the housing 19, and a hub attachment portion 48 integrally formed with a proximal end of the operation plate portion 46 and attached to the catheter hub 14 freely detachably manner.

The operation plate portion 46 is a portion where a user's finger is touched and advancing and retracting operation is performed. In the initial state, a pair of side edges 46a, 46b of the operation plate portion 46 is arranged at the pair of rail portions 42 and upper surfaces of the pair of side walls 34a, 34b on the proximal end sides of the rail portions 42. The operation plate portion 46 is formed thin enough to have flexibility capable of being curved in a direction orthogonal to a surface direction of the operation plate portion 46, more specifically, in a direction separating away from the inner needle 16. A constituent material of the operation plate portion 46 (catheter operation member 20) is not particularly limited and, for example, may be suitably selected from the materials exemplified for the catheter hub 14. Meanwhile, the portion extending along the catheter 12 (long portion) is not limited to the above-described plate portion, and various kinds of structures (such as a rod portion) may be applied.

An upper side rib 50 and tabs 52, 54 are provided on an upper surface of the operation plate portion 46, a distal end camber portion 56 is provided at a distal end of the operation plate portion 46, and a holding portion 58 and a lower side rib 51 are provided on a lower surface of the operation plate portion 46.

A plurality of upper side ribs 50 and a plurality of lower side ribs 51 are provided in a longitudinal direction of the operation plate portion 46. These upper and lower side ribs 50, 51 project upward and downward respectively and linearly extend in a width direction of the operation plate portion 46, thereby enhancing strength in the width direction of the operation plate portion 46. With this structure, the operation plate portion 46 is prevented from being bent, warped, or the like inside the housing 19 even when external force is applied from the outside, and advancing and retracting is smoothly performed along the upper surfaces of the pair of side walls 34a, 34b and the rail portions 42.

The tabs 52, 54 are portions provided assuming that the user's finger directly touches the same, and the tabs project higher than the upper side rib 50. The number of tabs 52, 54 to be provided is not limited to two illustrated in FIG. 2, and one tab or three or more tabs may be provided. In the case of providing two or more of the tabs 52, 54, preferably, the tabs are arranged at an interval larger than an interval of the ribs, and according to the present embodiment, the tabs are arranged at a position close to the distal end camber portion 56 and a position overlapping with a distal end of the hub attachment portion 48.

As illustrated in FIG. 6, the distal end camber portion 56 includes a thick portion 56a projecting to the lower surface side of the operation plate portion 46, and becomes gradually thinner from the thick portion 56a in the distal end direction while being curved upward. An insertion groove 57 through which the catheter 12 is made to pass in a non-contacting manner or with little friction is formed at a center portion in a width direction of the thick portion 56a. With advancement of the catheter operation member 20, a cambered lower surface side of the distal end camber portion 56 contacts the patient or is gripped by the user, thereby guiding the operation plate portion 46 to be directed obliquely upward.

On the other hand, a plurality of holding portions 58 of the catheter operation member 20 is provided in the longitudinal direction of the operation plate portion 46 (five holding portions in FIG. 6). The holding portions 58 are arranged at equal intervals in the longitudinal direction of the operation plate portion 46 and hold the catheter 12 at the respective positions by contacting the outer peripheral surface thereof. Meanwhile, the catheter operation member 20 may also have a structure in which one holding portion 58 is provided at a predetermined position to hold the catheter 12.

The plurality of holding portions 58 each includes a pair of projecting pieces 70 (projecting portions) projecting downward from the lower surface of the operation plate portion 46. The pair of projecting pieces 70 is symmetrically formed each other interposing an intermediate portion in the width direction of the operation plate portion 46 (in the following, a projecting piece 70 located on a near side in FIG. 6 will be also referred to as a first projecting piece 71 and a projecting piece 70 located on a far side in FIG. 6 will be also referred to as a second projecting piece 72).

As illustrated in FIG. 7, the first and second projecting pieces 71, 72 are formed in a rectangular shape that is wide in the width direction of the operation plate portion 46. An interval of respective inner edges of the first projecting piece 71 and the second projecting piece 72 is set slightly wider than the outer diameter of the catheter 12. Nail portions 73, 74 slightly projecting inward in the width direction are formed on lower portion sides of the respective inner edges. An interval of respective projecting ends of the pair of the nail portions 73, 74 is set slightly narrower than the outer diameter of the catheter 12 by projecting toward each other. Upper portions of the respective nail portions 73, 74 are formed as curved edges 73a, 74a approximate to or same as a curvature of the outer peripheral surface of the catheter 12.

When the catheter 12 is assembled to the catheter operation member 20, the catheter 12 passes the pair of nail portion 73, 74 and is easily nipped between the first and second projecting pieces 71, 72. The term "nip" in the present specification means a state that the holding portions 58 contact and hold the catheter 12 with weak engagement force. Needless to mention, the structure of the holding portion 58 is not limited to the above-described pair of the projecting pieces 70, and various kinds of structures to hold the catheter 12 are applicable. For example, the holding portion 58 may be the lower surface itself of the operation plate portion 46, or a groove or a recessed portion formed at a projecting portion projecting from the lower surface. Also, for example, the holding portion 58 may be a member adhesive to the catheter 12 by using a material having biocompatibility and a suitable adhesive property.

The pair of nail portions 73, 74 includes, on the lower side, taper portions 73b, 74b inclined upward toward to the inner side in the width direction. The taper portions 73b, 74b smoothly guide the catheter 12 to enter between the first and second projecting pieces 71, 72. Furthermore, the lower side rib 51 contacts the catheter 12 cooperatively working with the holding portions 58, and the catheter 12 is stably held near the respective nail portions 73, 74 separated from the lower surface of the operation plate portion 46.

Additionally, the first and second projecting pieces 71, 72 are formed in a square shape having round corners at protruding ends (lower ends) in side sectional view. The round corners of the first and second projecting pieces 71, 72 allow the support member 44 located on the lower side to easily climb over the first and second projecting pieces 71, 72 (improves slidability) when the catheter operation member 20 advances and retracts.

Moreover, as illustrated in FIG. 6, the first and second projecting pieces 71, 72 are formed in a projecting manner such that the projecting portions of each pair of projecting portion are offset from one another in the longitudinal direction of the operation plate portion 46. More specifically, the first projecting piece 71 is located more on the distal end side than the second projecting piece 72. Additionally, a proximal end surface of the first projecting piece 71 and a distal end surface of the second projecting piece 72 are provided at the same position in the longitudinal direction of the operation plate portion 46. In other words, the first projecting piece 71 and the second projecting piece 72 hold the catheter 12 with weak engagement force by not clamping the catheter 12 on the same axis. Therefore, when the operation plate portion 46 is curved, the catheter operation member 20 displaces and detaches hooked portions of the catheter 12 in the order of the first projecting piece 71 and the second projecting piece 72.

On the other hand, the hub attachment portion 48 of the catheter operation member 20 is formed in a box shape by a pair of side plates 60 projecting downward from the operation plate portion 46 and a semi-cylindrical upper plate 62 slightly projecting upward from the operation plate portion 46. In the case of viewing the hub attachment portion 48 from the lower direction, a proximal end side and an intermediate side of the pair of the side plates 60 extend in parallel and a distal end side continuous to the intermediate side is inclined inward in the distal end direction.

The catheter hub 14 is rotatably housed inside the pair of side plates 60 and the upper plate 62 while an attachment chamber 64 to inhibit axial movement of the catheter hub 14 relative to the hub attachment portion 48 is provided. The attachment chamber 64 is open to the outside at the lower portion and the proximal end of the hub attachment portion 48.

An inner surface of the attachment chamber 64 is formed with: a locking groove 66 formed by overlaying a trapezoid hole on a round hole; a groove portion 68 adapted to arrange the pair of side plates 60 and the upper plate 62 extending in a U-shape; and a pair of projections 69 projecting inside the hub attachment portion 48. The locking groove 66 allows the catheter 12 to pass through the trapezoid hole having a wide lower side and a narrow upper side, and arrange the catheter in the round hole, and appropriately locks the catheter 12 by hooking the same at a boundary portion between the trapezoid hole and the round hole. The groove portion 68 rotatably inhibits movement of the annular projection 28 of the catheter hub 14 in the distal end and proximal end directions and houses the same. Furthermore, the pair of projections 69 hooks the outer peripheral surface on the proximal end side of the catheter hub 14 with light engagement force.

With this structure, the hub attachment portion 48 keeps a locked state of the catheter 12 and the catheter hub 14 in the case of existing in the housing space 40 of the housing 19. On the other hand, when the catheter operation member 20 slips out from the housing 19 and the user lifts up the catheter operation member, thereby detaching the catheter hub 14 from the attachment chamber 64 and easily detaching the catheter 12 and the catheter hub 14.

Furthermore, as illustrated in FIG. 2, because the catheter assembly 10 supports the lower side of the catheter 12 held by the catheter operation member 20, the support member 44 is provided at the distal end side of the housing 19. The support member 44 includes: an axial rod portion 100 rotatably attached to the vertical pair of bearing holes 43*a*, 43*b* of the arrangement recessed portion 43; and a support body 102 projecting in a lateral direction from the axial rod portion 100 (in a direction orthogonal to an axial center of the axial rod portion 100) and formed in a predetermined shape.

In a state that the catheter operation member 20 is housed inside the housing 19, the support body 102 is induced by the axial rod portion 100 so as to be located inside the side wall 34*a*, namely, below the catheter 12 and stands by in a manner capable of supporting the catheter 12. With this structure, when downward pressing force directed downward is applied to the catheter operation member 20 by the user, the support member 44 supports the catheter 12 from the lower side and prevents the catheter 12 from being warped and suppresses the catheter 12 from slipping out from the holding portion 58. On the other hand, when the catheter operation member 20 slips out from the housing 19, the side plates 60 contact the support body 102 and make the support body 102 be rotated toward the outside of the side wall 34*a*. Consequently, the support member 44 smoothly detaches the catheter hub 14 and the needle protection member 26 from the housing 19.

The catheter assembly 10 according to the present embodiment has the basic structure as described above, and functions and effects thereof will be described below.

As described above, the catheter assembly 10 is used to construct an introducing portion for transfusion to a patient. In the initial state illustrated in FIG. 1, the catheter hub 14, auxiliary member hub 24, and needle protection member 26 are connected, and the catheter hub 14 is housed in the attachment chamber 64 of the catheter operation member 20 (hub attachment portion 48) and integrally housed in the housing space 40 of the housing 19.

Figure 8A:
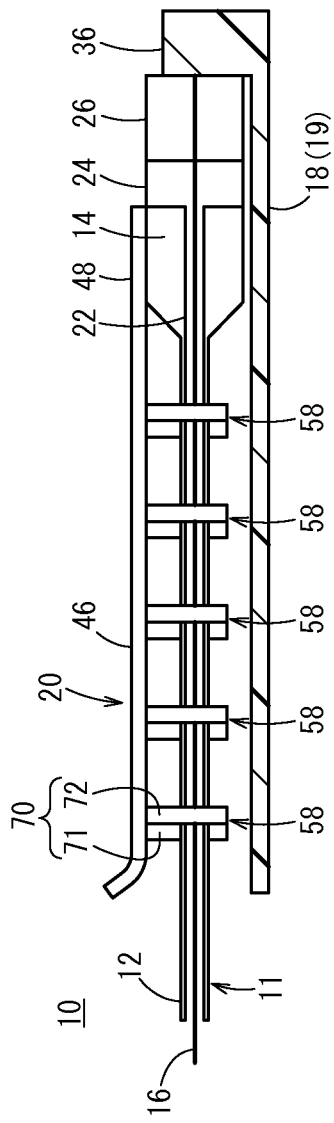
FIG. 8A is a schematic diagram illustrating a holding state of a holding portion at the time of puncture with the catheter assembly in FIG. 1.

Furthermore, in the initial state, the multiple tube unit 11 is held by the plurality of holding portions 58 of the catheter operation member 20 as illustrated in FIG. 7. Each of the holding portions 58 nips the outer peripheral surface of the catheter 12 with weak engagement force in each position in the axial direction, and the catheter 12 is firmly held as the entire catheter operation member 20. Additionally, the operation plate portion 46 keeps linearity by being arranged in the pair of side walls 34*a*, 34*b* and rail portions 42 of the housing 19. Therefore, the multiple tube unit 11 is properly held in a state extending linearly inside the housing 19 as illustrated in FIG. 8A.

At the time of using the catheter assembly 10, the user grips and operates the housing 19, and punctures a patient with the multiple tube unit 11. At the time of puncture, the holding portions 58 hold the catheter 12, thereby preventing the multiple tube unit 11 from being warped inside the housing 19 even when resistance force is received along with puncture. In other words, the holding portions 58 aligned in the axial direction of the operation plate portion 46 keep holding the multiple tube unit 11 while decentralizing the resistance force. In addition, at the time of puncture, the distal end side of the catheter operation member 20 is pressed downward by the user, and the multiple tube unit 11 is supported by the support member 44 from lower side. Therefore, the multiple tube unit 11 is fixed between the support member 44 and the catheter operation member 20 (insertion groove 57 of the distal end camber portion 56), and transmission of the resistance force at the time of puncture can be more suppressed.

As a result, the extending state of the multiple tube unit 11 from the distal end of the housing 19 is properly kept, and the user can puncture the patient with the multiple tube unit 11 without feeling any discomfort. Furthermore, the catheter assembly 10 can be formed thinner by reducing strength of the inner needle 16, and burden on the patient can be reduced.

As illustrated in FIG. 3A, in a puncture state with the multiple tube unit 11, the user makes the catheter 12 advance relative to the inner needle 16 and inserts the same into a blood vessel. At this point, the user puts a finger on the upper side rib 50 or the tabs 52, 54 of the catheter operation member 20 and slides the catheter operation member 20 in the distal end direction relative to the housing 19. In advancing operation of the catheter operation member 20, the multiple tube unit 11 is kept being held by the holding portions 58, and the catheter 12 smoothly advances. Furthermore, during the advancing operation, the lower side of the multiple tube unit 11 can be supported by the support member 44, and the multiple tube unit 11 is prevented from being warped downward. Therefore, even though the catheter 12 receives reaction force from skin and the like at the time of inserting the catheter 12, the multiple tube unit 11 can be prevented from being warped. For example, the needle tip 16a of the inner needle 16 is prevented from retracting and slipping out from the skin by being warped, and inconvenience such as puncturing the skin again with the inner needle 16 can be avoided.

Figure 8B:
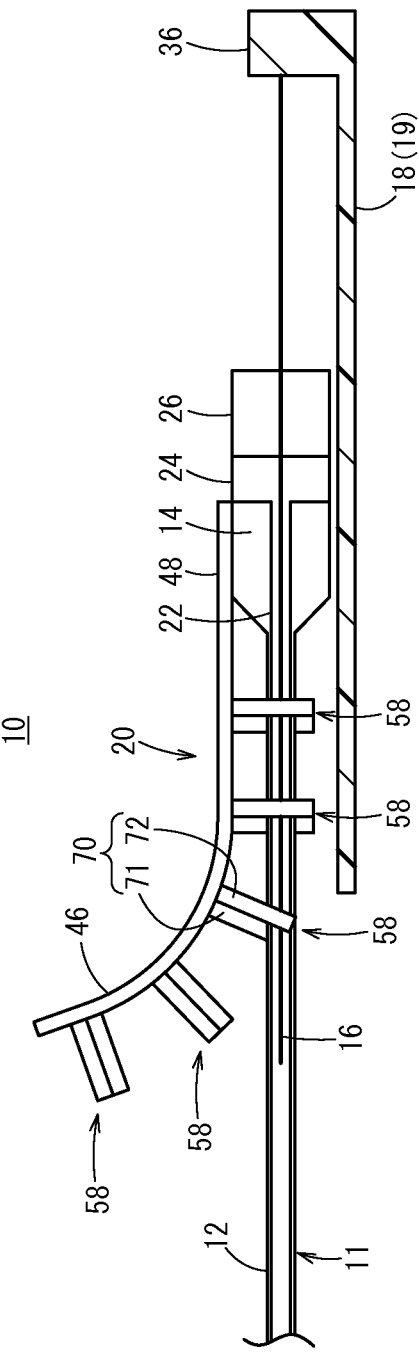
FIG. 8B is a schematic diagram illustrating a state of the holding portion at the time of performing advancing operation of the catheter operation member in FIG. 1.

When the distal end camber portion 56 contacts the patient's skin along with advancement in the distal end direction or when the user grips the distal end camber portion 56 or the like, the operation plate portion 46 of the catheter operation member 20 is curved in a manner separating away from the axial direction of the multiple tube unit 11 as illustrated in FIG. 8B. The operation plate portion 46 is curved from the distal end side of the operation plate portion 46, and the holding portions 58 aligned in the longitudinal direction sequentially detach the multiple tube unit 11 from the distal end side against respective engagement force. Even in the case where holding by the holding portion 58 on the distal end side is released due to curving of the operation plate portion 46, the holding portion 58 on the proximal end side where linearity is kept inside the housing 19 continues holding the multiple tube unit 11. Additionally, the offset first and second projecting pieces 71, 72 of the holding portions 58 unhook the hooked catheter 12 in the order of the first projecting piece 71 and the second projecting piece 72, thereby detaching the multiple tube unit 11 while suppressing impact applied thereto.

Here, in the case where the user cannot insert the catheter 12 smoothly, the user can once perform retracting operation for the catheter operation member 20 and may make the catheter 12 retract relative to the inner needle 16 and the housing 19. At the time of retraction, the operation plate portion 46 is housed again in the rail portions 42 of the housing 19 and the curved state is changed to the linear state (non-curved state). At this point, the support member 44 pushes up the catheter 12 toward the holding portions 58, and also the taper portions 73b, 74b of the nail portions 73, 74 guide the catheter 12 between the pair of projecting pieces 70. Consequently, the catheter 12 is sequentially nipped by the plurality of holding portions 58.

With advancement of the catheter operation member 20 (or with retraction of the inner needle 16 and the housing 19), the catheter hub 14 attached to the hub attachment portion 48 and the needle protection member 26 attached to the catheter hub 14 also advance. Furthermore, when the catheter hub 14 and the needle protection member 26 slip out from the housing 19 and advance to some extent, the needle tip 16a of the inner needle 16 is housed inside the needle protection member 26. The needle protection member 26 inhibits the needle tip 16a from slipping out by the slip-out stop member 94, and also prevents the needle tip 16a from being exposed again by opening, in front of the needle tip 16a, the shutter 82 that has been closed by the outer peripheral surface of the inner needle 16 inside the needle protection member 26.

Furthermore, after the catheter hub 14 is detached from the housing 19, engagement between the locking groove 66, pair of grooves 69 of the hub attachment portion 48, and catheter hub 14 can be easily released. Therefore, the user separates the catheter operation member 20 from the catheter 12 and the catheter hub 14 at appropriate timing. Consequently, the catheter 12 and the catheter hub 14 are properly indwelled in the patient.

As described above, in the catheter assembly 10 according to the first embodiment, the holding portions 58 of the catheter operation member 20 directly hold the catheter 12 in a freely detachable manner. Therefore, the catheter 12 and the inner needle 16 can be prevented from being warped while mobility of the catheter 12 is surely secured. More specifically, the catheter operation member 20 properly keeps the extending state of the catheter 12 by directly holding the catheter 12 inside the housing 19, and prevents the catheter 12 from being warped even in the case of receiving resistance force at the time of puncture with the multiple tube unit 11. Therefore, the user can properly puncture the patient with the multiple tube unit 11, which is prevented from being warped, without feeling any discomfort. Furthermore, the catheter operation member 20 can smoothly make the catheter 12 being held advance and retract relative to the inner needle 16 and the housing 19.

In this case, because the operation plate portion 46 has flexibility, the catheter operation member 20 is curved when the user performs the advancing operation, and inconvenience such as interfering with the patient and making advancement difficult is avoided. Because the operation plate portion 46 is inhibited from being curved in the state of being housed inside the housing 19 and engaged with the housing 19, the operation plate portion can smoothly advance and retract inside the housing 19, and also the catheter 12 can be stably held by the holding portions 58. Furthermore, the catheter assembly 10 can easily perform holding and holding release of the catheter 12 with the holding portions 58 based on change between the curved state and the non-curved state of the operation plate portion 46. Moreover, because the operation plate portion 46 holds the catheter 12 in a manner formed in the linear shape in the width direction, the operation plate portion 46 is prevented from being warped, twisted, dropped, and the like inside the housing 19, and the catheter 12 can be more stably held by the holding portions 58.

Additionally, because the plurality of holding portions 58 is provided in the axial direction of the catheter 12, the catheter operation member 20 can firmly hold the entire catheter 12 even though holding force of each holding portion 58 is weak. Furthermore, the catheter operation member 20 sequentially releases the catheter 12 held by the holding portions 58 from the distal end side. Therefore, even in the case of receiving reaction force at the time of inserting the catheter 12, the catheter 12 can be held by the holding portion 58 on the proximal end side, and insertion of the catheter 12 can be smoothly continued.

Furthermore, when the catheter 12 is inserted between the first and second projecting pieces 71, 72 of the holding portion 58, the catheter 12 can be held with suitable engagement force in a contacting manner. Moreover, because the projecting portions of each pair of projecting pieces 71, 72 are offset from one another, engagement force of the first and second projecting pieces 71, 72 relative to the catheter 12 can be easily let out, and the catheter 12 can be prevented from being vibrated and the like at the time of holding release. Additionally, the catheter operation member 20 holds not only the catheter 12 but also the catheter hub 14 with the hub attachment portion 48. Therefore, operation force applied to the catheter operation member 20 from the user can be more surely transmitted to the catheter 12 and the catheter hub 14.

Note that the catheter assembly 10 according to this embodiment of the present invention is not limited to the above-described embodiment, and various kinds of application examples and modified examples are applicable. For example, the catheter assembly 10 may have a structure in which a guide wire not illustrated is housed in the through-hole 16b of the inner needle 16, and the guide wire is exposed from the needle tip 16a to guide the catheter 12 by controlling a guide wire operation member not illustrated and connected to the guide wire.

Second Embodiment

Next, a catheter assembly 200 according to a second embodiment of the present invention will be described. Note that a reference sign same as the one used in a first embodiment has the same structure or the same function in the embodiment described below, and a detailed description therefor will be omitted.

Figure 9:
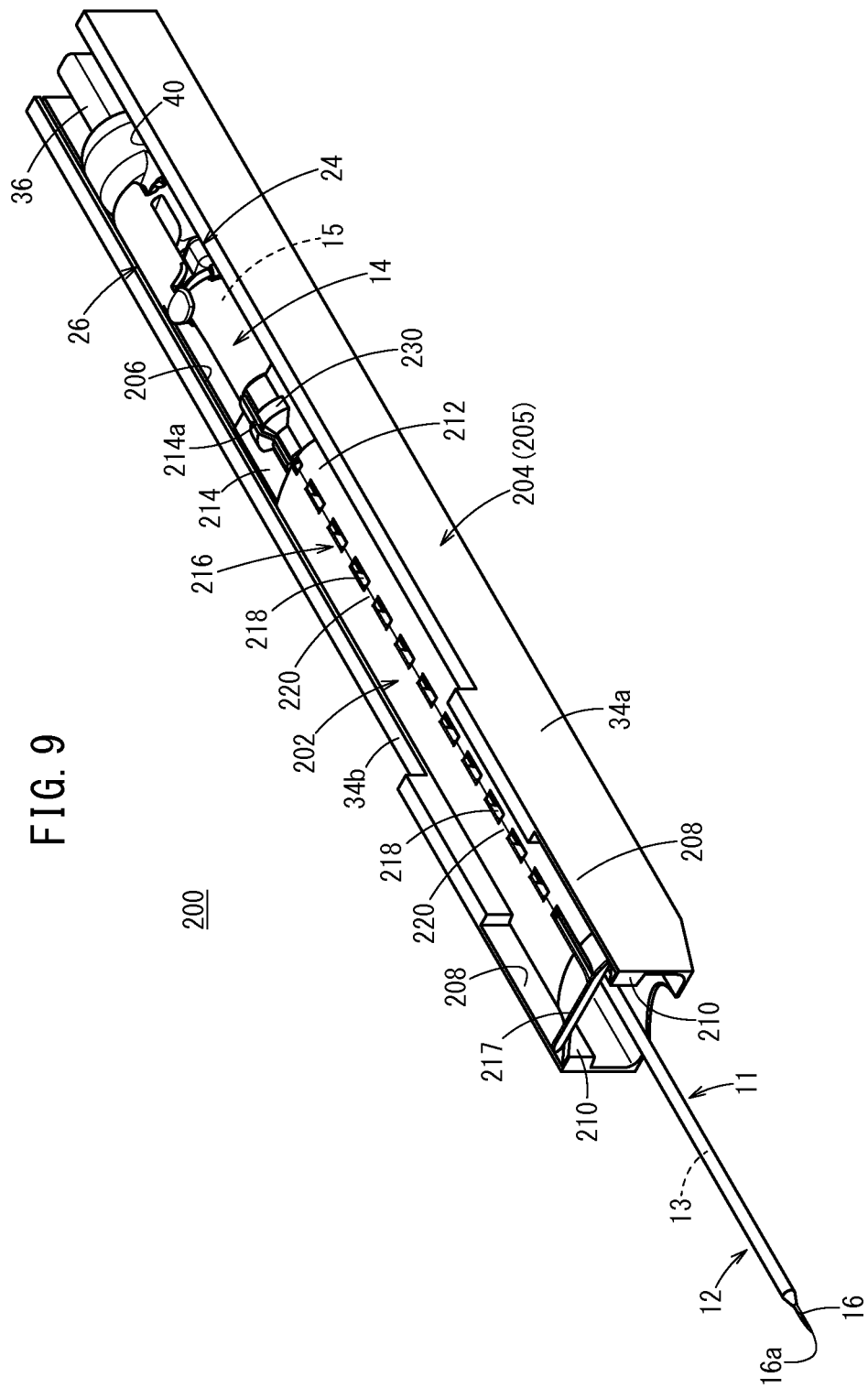
FIG. 9 is a perspective view illustrating an entire structure of a catheter assembly according to a second embodiment of the present invention.

The catheter assembly 200 according to the second embodiment differs from a catheter assembly 10 according to the first embodiment in that a catheter operation member 202 is bent in an initial state in which the catheter operation member 202 is housed in a needle hub 204 as illustrated in FIG. 9. Furthermore, the catheter assembly 200 has a structure in which a support member 44 in FIG. 1 is not provided and a catheter 12 (multiple tube unit 11) is held and supported only by the catheter operation member 202.

Figure 10A:
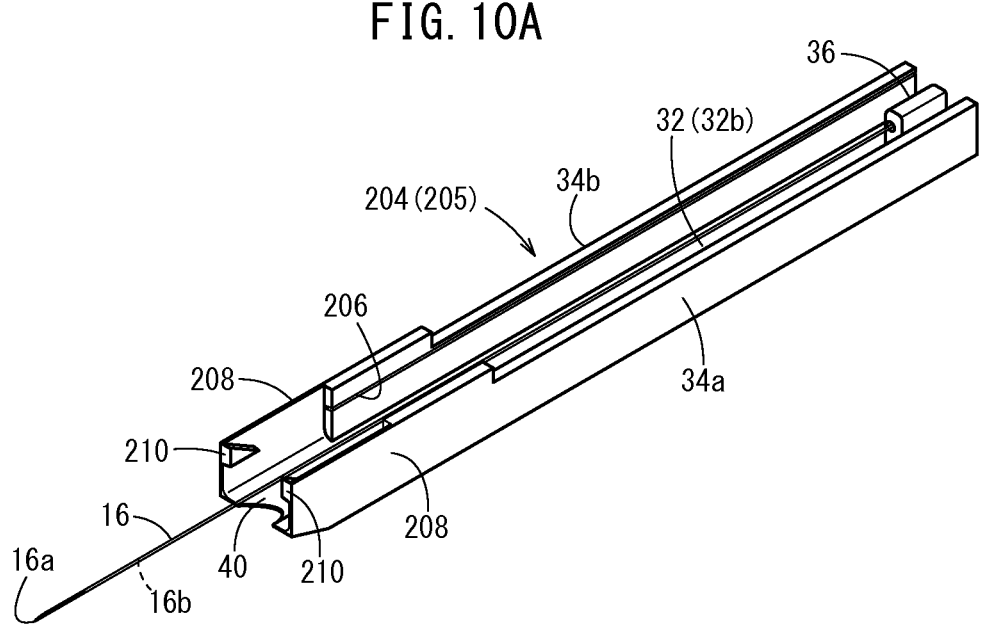
FIG. 10A is a perspective view illustrating a housing of the catheter assembly in FIG. 9.
Figure 10B:
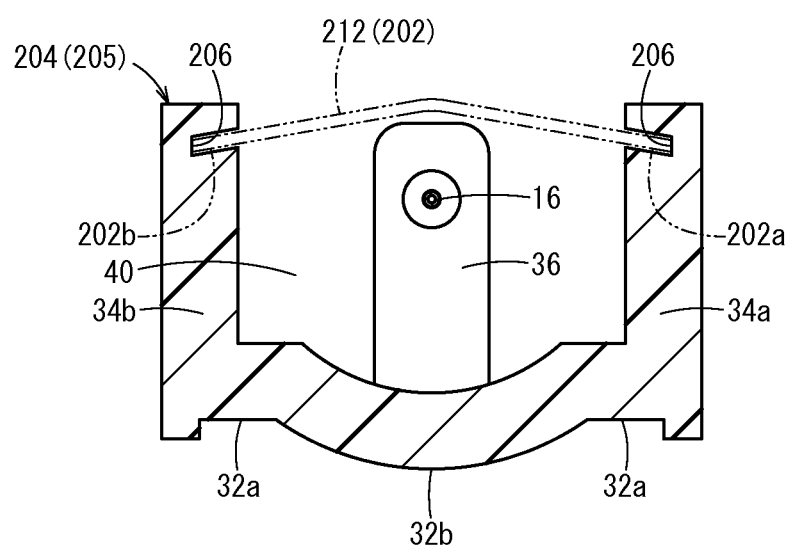
FIG. 10B is a front sectional view of the housing.

As illustrated in FIGS. 10A and 10B, because the needle hub 204 houses a whole portion of side edges 202a, 202b of the catheter operation member 202 in the housing space 40 in the initial state, the needle hub 204 is formed as a housing 205 including a groove-like rail portion 206 extending long in a longitudinal direction in each of a pair of side walls 34a, 34b. In a cross-sectional view, the pair of rail portions 206 is carved obliquely downward from inner surfaces of the side walls 34a, 34b toward the outside, and induces the catheter operation member 202 to be curved between the pair of side walls 34a, 34b. Meanwhile, the housing 205 may be provided with a bridge portion or a lid body not illustrated on a more upper side than the rail portion 206 in order to inhibit the curved catheter operation member 202 from slipping out upward.

Furthermore, the rail portion 206 is not provided and a pair of thin portions 208 formed by being cut off thin is formed on a distal end side of the pair of side walls 34a, 34b. In a side surface view, a triangle-shaped guiding projection 210 (guide portion) is formed in a projecting manner on each of inner surfaces of the pair of thin portions 208 in order to guide the catheter operation member 202 obliquely upward.

Figure 11A:
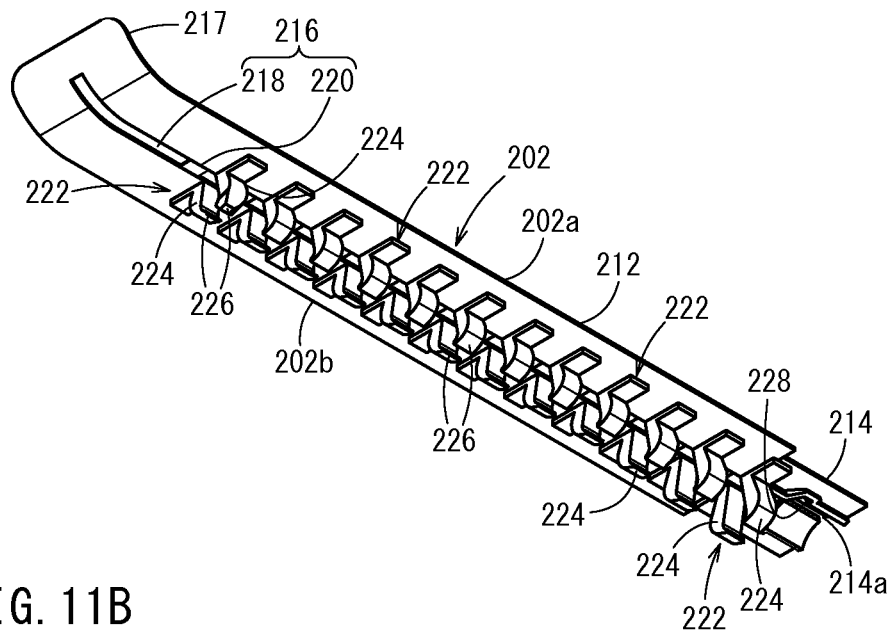
FIG. 11A is a perspective view illustrating a catheter operation member of the catheter assembly in FIG. 9.

On the other hand, as illustrated in FIGS. 9 and 11A, the catheter operation member 202 includes: an operation plate portion 212 (long portion) not provided with an upper side rib 50, a lower side rib 51, and a tab 52; and a hub attachment portion 214 formed thinner than a hub attachment portion 48 according to the first embodiment. A bendable portion 216 that allows the operation plate portion 212 to be curved is provided at a center portion in a width direction of the operation plate portion 212. The bendable portion 216 includes: a rectangle-shaped bore 218 penetrating an upper and lower surfaces of the operation plate portion 212; and a connecting portion 220 provided between adjacent bores 218 and formed thinner than a plate thickness of the operation plate portion 212.

The plurality of bores 218 is provided at equal intervals in a longitudinal direction of the operation plate portion 212. Furthermore, the bore 218 located on the most distal end is formed long from the operation plate portion 212 to a distal end camber portion 217 formed to have a thin plate thickness. The bendable portion 216 formed of the plurality of bores 218 and the connecting portion 220 can elastically deform the operation plate portion 212 into a bent shape in a front sectional view illustrated in FIGS. 11B and 11C. Meanwhile, the hub attachment portion 214 includes a slit 214a at a center portion in a width direction corresponding to the bendable portion 216.

Furthermore, a plurality of holding portions 222 provided in the longitudinal direction of the operation plate portion 212 is formed of a pair of hooks 224 (projecting portions) projecting downward in a front view as illustrated in FIG. 11A. Meanwhile, the holding portions 222 are provided at positions same as the plurality of bores 218 in the longitudinal direction in a manner interposing the bores 218. The pair of hooks 224 is located adjacent to the bore 218 at an upper end portion connected to the operation plate portion 212, and once gradually widened outward in the width direction from upper end portions thereof to a lower side and then curved inward from a middle position thereof. A nail portion 226 projecting short inward is provided at a lower end portion of the hook 224.

Figure 11B:
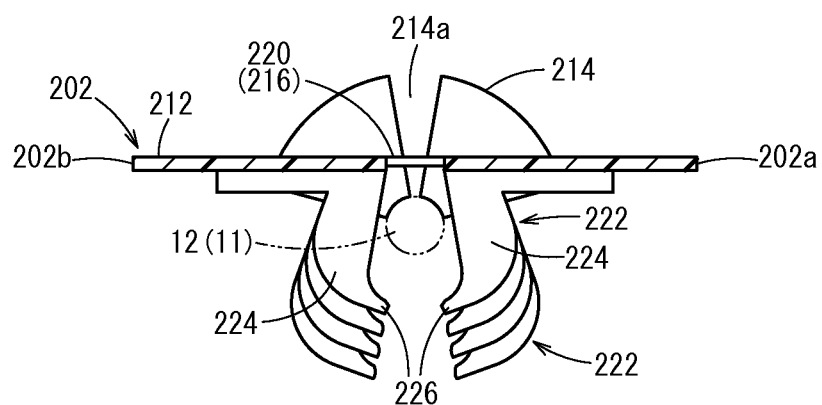
FIG. 11B is a front sectional view of the catheter operation member.
Figure 11C:
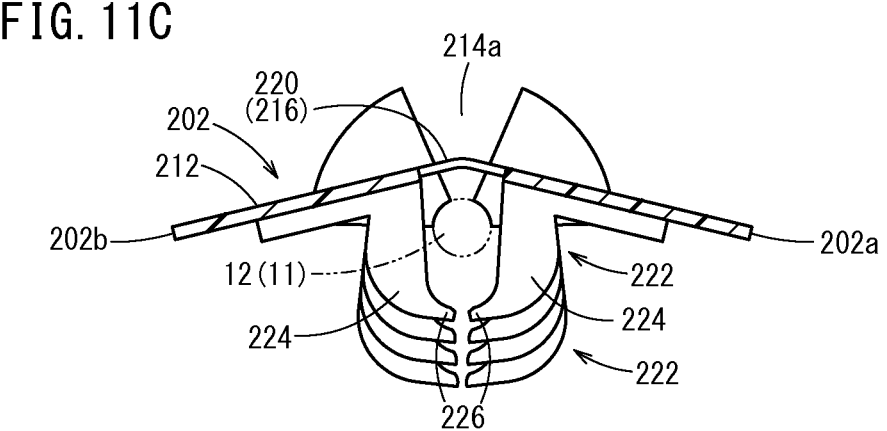
FIG. 11C is a front sectional view of the catheter operation member in a housing state in the housing.

The nail portions 226 of the pair of hooks 224 are separated from each other when the operation plate portion 212 is in a non-curved state illustrated in FIG. 11B while the nail portions 226 come close to each other when the operation plate portion 212 is in a curved state illustrated in FIG. 11C. In the curved state, the pair of nail portions 226 has a width narrower than an outer diameter of the catheter 12 and hooks the catheter 12. More specifically, the operation plate portion 212 is curved in a state of being housed in the housing 205, thereby the plurality of holding portion 222 of the catheter operation member 202 firmly holding the catheter 12 (multiple tube unit 11).

Meanwhile, the holding portions 222 (pair of hooks 224) aligned on the proximal end side are formed in a manner gradually becoming larger as a position approaches in the proximal end direction. The pair of hooks 224 located on the most proximal end side can clamp a distal end portion of a catheter hub 14 having a tapered shape. The holding portions 222 on the proximal end side function to hold a proximal end portion of the catheter 12 close to the catheter hub 14 even when the operation plate portion 212 is gently curved at the time of assembling the catheter assembly 200, and assembly is simplified.

Furthermore, the hub attachment portion 214 is formed in a shape obtained by cutting a cylinder, and has a structure to partly cover the distal end side of the catheter hub 14. A bulging portion 230 including a housing groove 228 capable of housing an annular projection 28 of the catheter hub 14 is provided at an intermediate portion in a front-back direction of the hub attachment portion 214. The hub attachment portion 214 is attached to the catheter hub 14 in a manner freely advancing and retracting in a longitudinal direction of the housing 205 and a freely detachable manner by housing the annular projection 28 in the housing groove 228 and covering the upper side of the catheter hub 14. In the case of moving to the thin portion 208 from the rail portions 206 of the pair of side walls 34*a*, 34*b*, the hub attachment portion 214 can be detached from the housing 205.

The catheter assembly 200 according to the second embodiment is basically formed as described above, and functions and effects thereof will be described below.

As for the catheter assembly 200, a patient is punctured with the catheter 12, an auxiliary member 22, and the multiple tube unit 11 of an inner needle 16 under control of a user same as the catheter assembly 10 according to the first embodiment. Because the catheter operation member 202 housed in the housing 205 is in the curved state at the time of puncture as illustrated in FIGS. 10B and 11C, the multiple tube unit 11 is held by narrowing a space between the pair of nail portions 226 in each of the holding portions 222 aligned in the longitudinal direction of the catheter operation member 202. With this structure, the multiple tube unit 11 is prevented from being warped inside the housing 205, and the user can perform puncture with the multiple tube unit 11 without any discomfort.

Additionally, the user performs advancing operation of the catheter operation member 202 in a distal end direction in a puncturing state with the multiple tube unit 11. At the time of advancement, the distal end camber portion 217 and the operation plate portion 212 are guided by the pair of guiding projections 210 (guide portions) of the housing 205 so as to be directed obliquely upward, and when the distal end camber portion and the operation plate portion are let out from the housing 205, the operation plate portion 212 is elastically restored and the curved state is changed to the non-curved state. During this state change, the pair of nail portions 226 actuates so as to be separated from each other and releases the catheter 12 from being held. More specifically, the catheter operation member 202 sequentially detaches the catheter 12 from the pair of hooks 224 on the distal end side near the pair of the guiding projections 210 where the operation plate portion 212 is directed obliquely upward. Even after the catheter 12 is thus detached from the distal end side, the pair of hooks 224 on the proximal end side continues holding the catheter 12. Therefore, the catheter assembly 200 prevents the advancing catheter 12 from being warped even in the case of receiving reaction force from the patient, and the catheter 12 is smoothly inserted into a blood vessel.

As described above, in the catheter assembly 200 according to the second embodiment also, effects same as the catheter assembly 10 according to the first embodiment can be obtained. Particularly, in the holding portions 222 of the catheter assembly 200, because the operation plate portion 212 is curved in a bent shape, the pair of hooks 224 comes close to each other, and the catheter 12 can be surely held by the holding portions 222. Additionally, in this structure, the catheter 12 is automatically detached from the holding portions 222 by changing the operation plate portion 212 from the curved state to the non-curved state. Therefore, holding release of the catheter 12 can be smoothly performed.

Furthermore, because the operation plate portion 212 includes the bendable portion 216, the operation plate portion 212 is easily formed in the bent shape having a top at the center portion in the width direction of the operation plate portion 212, and the catheter 12 can be stably held by the holding portions 222. Moreover, because the housing 205 includes the pair of guiding projections 210, the catheter operation member 202 is easily curved when the advancing operation in the distal end direction is performed. As a result, the catheter assembly 200 can separate the catheter 12 from the operation plate portion 212 while detaching the catheter 12 from the holding portions 222.

Figure 12:
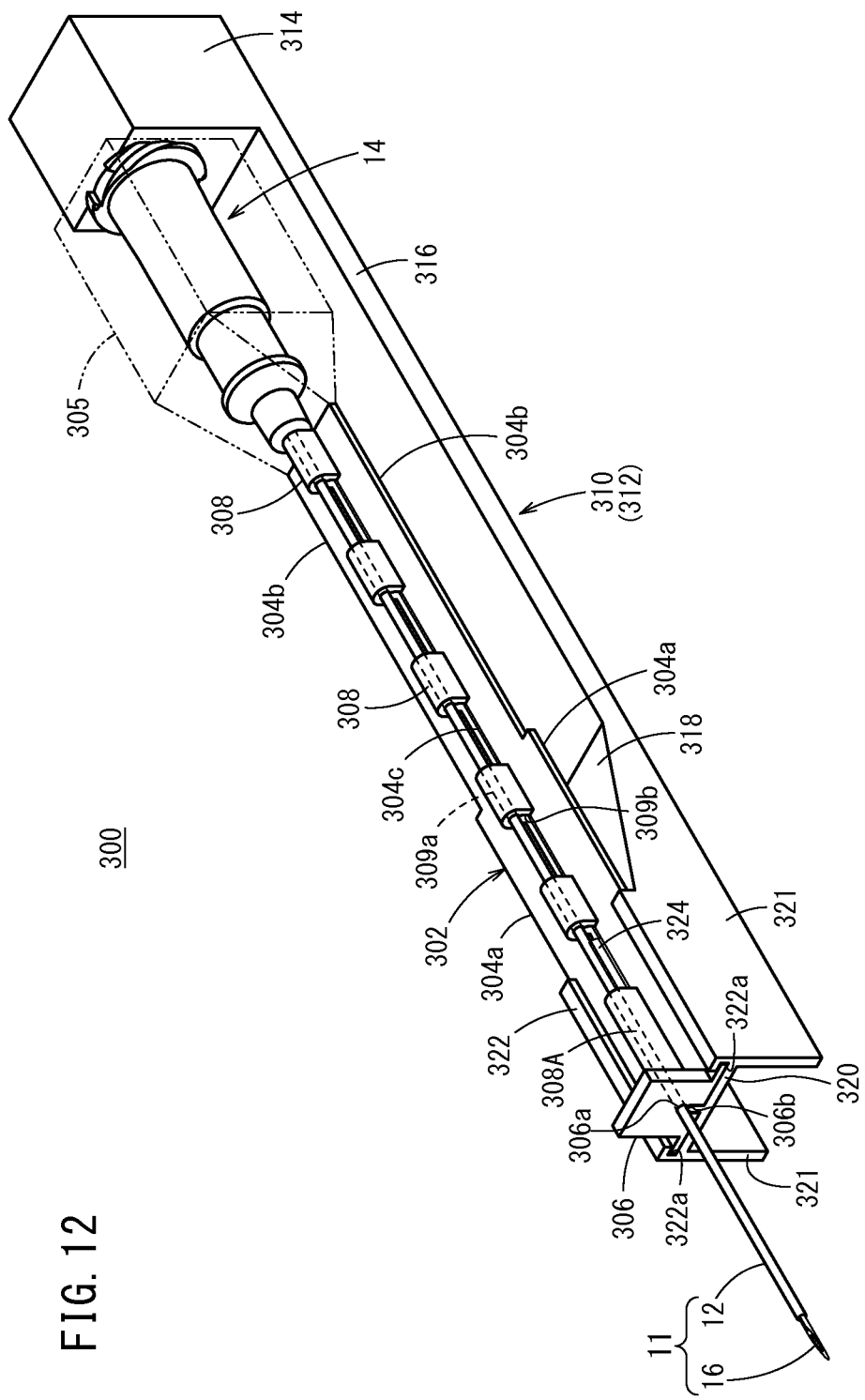
FIG. 12 is a perspective view illustrating an entire structure of a catheter assembly according to a third embodiment of the present invention.

Next, a catheter assembly 300 according to a third embodiment of the present invention will be described. As illustrated in FIG. 12, the catheter assembly 300 differs from catheter assemblies 10, 200 according to first and second embodiments in that a holding portion 308 of a catheter operation member 302 is arranged on an upper surface side of an operation plate portion 304. Meanwhile, the catheter assembly 300 has a structure not including an auxiliary member 22, an auxiliary member hub 24, and a needle protection member 26 described above, but needless to mention that the respective component may be also included.

The catheter operation member 302 includes the operation plate portion 304 (long portion) formed in a flat plate shape, and a tub 306 and a plurality of holding portions 308 are provided on the upper surface of the operation plate portion 304. The operation plate portion 304 includes a wide side edge 304*a* formed from an axial middle position in a distal end direction, and includes a side edge 304*b* narrower than the side edge 304*a* formed from an intermediate portion in the axial direction in a proximal end direction. Furthermore, a lower surface of the operation plate portion 304 is formed flat. A slit 304*c* adapted to divide the operation plate portion 304 in a width direction is formed at an intermediate portion in the width direction of the operation plate portion 304.

Figure 13:
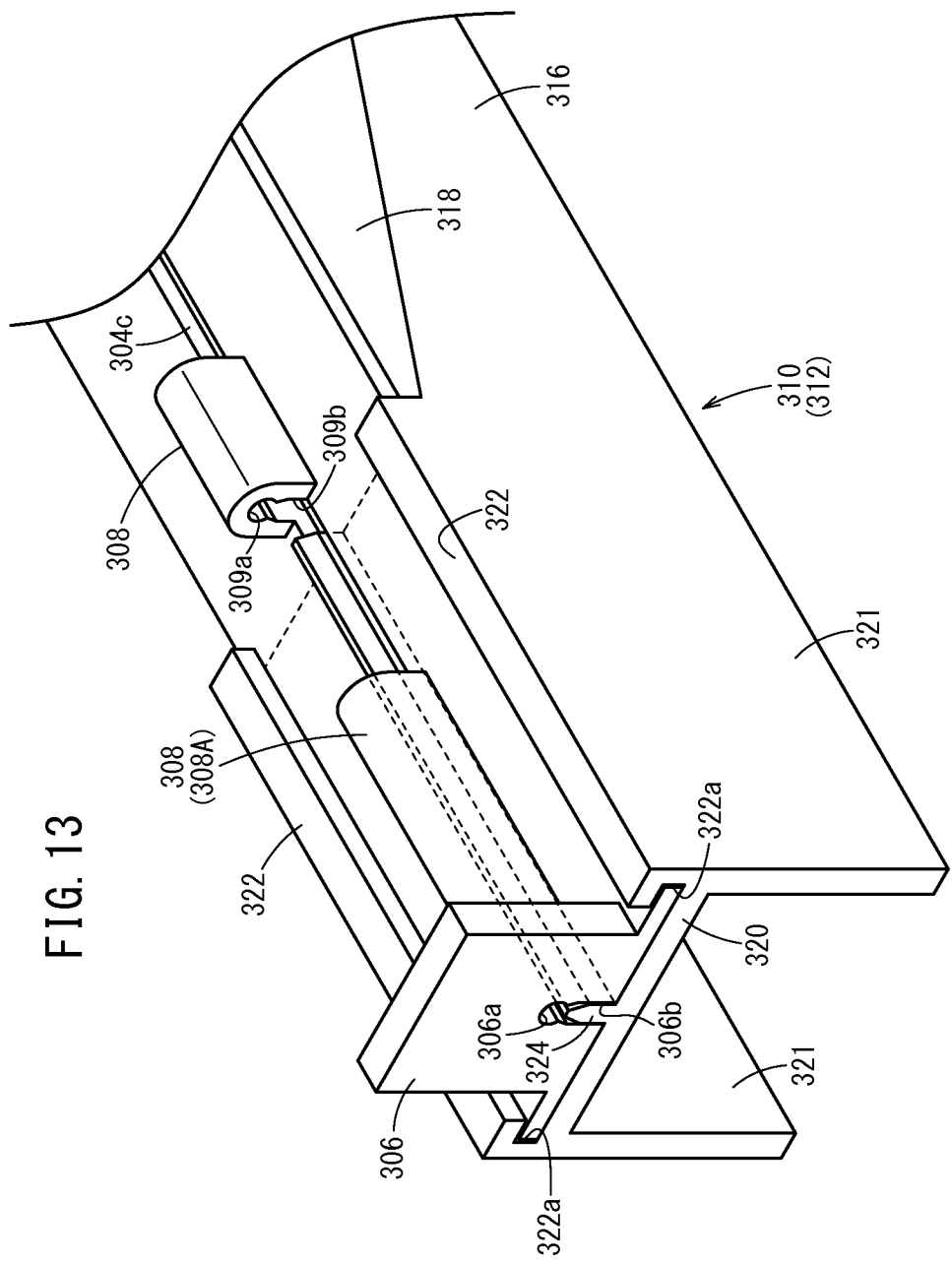
FIG. 13 is a perspective view illustrating enlarged distal end portions of a catheter operation member and a needle hub in FIG. 12.

The tub 306 is provided at a distal end of the operation plate portion 304 and formed in a manner projecting upward. As illustrated in FIG. 13, a mouth portion for catheter 306*a* to pass a catheter 12 and a mouth portion for projection 306*b* in communication with the mouth portion for catheter 306*a* are provided in the vicinity of a place where the tub 306 is connected to the operation plate portion 304. The mouth portion for catheter 306*a* is in communication with a holding hole 309*a* of a holding portion 308A continued to a proximal end surface of the tub 306. The mouth portion for projection 306*b* is in communication with a hole for projection 309*b* of the holding portion 308A.

The holding portion 308 has a function to hold the catheter 12 and an inner needle 16 (multiple tube unit 11). The holding portion 308 projects in an arc shape from the upper surface of the operation plate portion 304 and forms a bridge for the operation plate portion 304 divided in the width direction by the slit 304*c*. Furthermore, the holding portions 308 are provided at equal intervals in a longitudinal direction (axial direction) of the operation plate portion 304. The holding portion 308A on the distal end side is connected to the tub 306 and extends slightly longer compared to other holding portions 308.

The holding hole 309*a* adapted to hold the catheter 12 and the hole for projection 309*b* in communication with the holding hole 309*a* and in communication with the slit 304*c* are provided inside the holding portion 308. The holding hole 309*a* is formed in a round shape in a front view, and the hole for projection 309*b* is formed in a trapezoid in the front view. A vicinity of a boundary where the holding hole 309*a*, which is in communication with the hole for projection 309*b*, is formed narrow in order to hold the catheter 12.

Because the plurality of holding portions 308 holds the catheter 12 with suitable engagement force, operation force of a user applied to the catheter operation member 302 is directly transmitted to the catheter 12 and makes the catheter 12 and the catheter hub 14 advance and retract. Furthermore, the catheter 12 extends to a position higher than the operation plate portion 304 in a holding state by the holding portions 308.

Furthermore, the catheter hub 14 is arranged on the proximal end side of the catheter operation member 302, and the inner needle 16 passes through the catheter hub 14. Because the catheter 12 and the inner needle 16 are held by the plurality of holding portions 308, the catheter operation member 302 makes the catheter hub 14 stand by at an extending portion of the inner needle 16. Meanwhile, the catheter operation member 302 includes a hub attachment portion 305 adapted to detachably hold the catheter hub 14 and transmit, to the catheter hub 14, operation force of the catheter operation member 302 by the user (refer to dot-and-dash lines in FIG. 12).

On the other hand, a needle hub 310 has a long plate shape wider and axially longer than the catheter operation member 302. Furthermore, the needle hub 310 is formed to have a plate thickness thicker than that of the catheter operation member 302 and non-bendable rigidity. Therefore, the needle hub is formed as a grip portion 312 to be gripped by the user at the time of puncture with the multiple tube unit 11. The grip portion 312 exposes the catheter 12 and the catheter hub 14 on the upper side, different from housings 19, 205 of the first and second embodiments.

The grip portion 312 includes a needle holding portion 314 to hold the inner needle 16, a barrel portion 316 extending from the needle holding portion 314 in a longitudinal direction, an inclined portion 318 continued to a distal end side of the barrel portion 316, and a support portion 320 continued to a distal end side of the inclined portion 318. The inclined portion 318 is inclined upward in the distal end direction. The support portion 320 extends in parallel to the barrel portion 316 at a position supporting a lower side of the catheter operation member 302. Furthermore, a pair of side walls 321 is provided on both sides in a width direction of the inclined portion 318 and the support portion 320, and the pair of side walls 321 is formed up to a lower end of the barrel portion 316, thereby providing a structure that can be clamped with user's fingers.

A pair of elongated projecting pieces 322 is formed on both sides in a width direction of the support portion 320 in a manner projecting upward. Rail portions 322a adapted to slidably arrange the side edge 304a of the catheter operation member 302 are provided on facing inner surfaces of the pair of elongated projecting pieces 322. With this structure, the support portion 320 is engaged with the operation plate portion 304 on the distal end side of the catheter assembly 300 in an initial state, and the grip portion 312 and the catheter operation member 302 are made in a non-separable state. Furthermore, a projection 324 is provided at a center portion in a width direction of the support portion 320. The projection 324 is inserted into the slit 304c and the hole for projection 309b of the catheter operation member 302, thereby supporting a lower side of the catheter 12 held by the catheter operation member 302. With this structure, the catheter 12 is arranged higher than the pair of elongated projecting pieces 322 in the initial state.

The catheter assembly 300 according to the third embodiment has the basic structure as described above, and functions and effects hereof will be described below.

According to the catheter assembly 300, a patient is punctured with the multiple tube unit 11 (catheter 12 and inner needle 16) under the control of a user. At the time of puncture, as illustrated in FIG. 12, the multiple tube unit 11 is interposed between the support portion 320 provided on the distal end side of the grip portion 312 and the catheter operation member 302, thereby holding the multiple tube unit 11. More specifically, a periphery of the catheter 12 is surrounded by the tub 306 and the holding portions 308 while the projection 324 supports the multiple tube unit 11 from the lower side, thereby preventing the multiple tube unit 11 from being warped, and the user can perform puncture with the multiple tube unit 11 without any discomfort.

The user pinches the tub 306 and the like of the catheter operation member 302 and performs advancing operation in the distal end direction in the puncturing state with the multiple tube unit 11. Consequently, the operation plate portion 304 is guided by the upper surface of the support portion 320 and the rail portions 322a, and moves linearly. Then, when the operation plate portion 304 is let out from the distal end of the grip portion 312 at the time of advancement, the operation plate portion 304 is curved in a direction separating away from the inner needle 16 along with user's operation or contact with a patient. In the plurality of holding portions 308, the plurality of holding portions 308 sequentially detaches the catheter 12 from the holding holes 309a due to curving of the operation plate portion. Even after the catheter 12 is detached from the distal end side, the holding portion 308 on the proximal end side continues holding the catheter 12. Therefore, the catheter assembly 300 prevents the advancing catheter 12 from being warped even in the case of receiving reaction force from the patient, and the catheter 12 is smoothly inserted in to a blood vessel.

Furthermore, when the catheter hub 14 reaches the inclined portion 318 at the time of insertion, the catheter operation member 302 is detached from the rail portions 322a while being guided obliquely relative to the grip portion 312, and large curving of the catheter operation member 302 is allowed. Consequently, separation of the catheter 12 and the catheter hub 14 from the catheter operation member 302 is urged.

As described above, in the catheter assembly 300 according to the third embodiment also, effects same as the catheter assemblies 10, 200 can be obtained. In short, the structure of the needle hub 310 where the catheter 12, catheter hub 14, and catheter operation member 302 are arranged is not particularly limited. For example, in the needle hub 310, there is no space between the lower surface of the catheter operation member 302 and the upper surface of the barrel portion 316. In other words, the needle hub 310 may have a structure having a long plate shape that slidably supports the lower surface of the catheter operation member 302.

What is claimed is:

1. A catheter assembly, comprising:
a hollow catheter;
a catheter hub configured to fix and hold the catheter;
an inner needle including a needle tip and configured to be removably inserted through an inside of the catheter;
a needle hub configured to fix and hold the inner needle; and
a catheter operation member capable of moving the catheter relative to the inner needle,
wherein the catheter operation member includes a holding portion configured to directly hold the catheter in a detachable manner.

2. The catheter assembly according to claim 1, wherein:
the catheter operation member extends in a longitudinal direction of the needle hub and includes an elongated portion that includes the holding portion, and
the elongated portion is curvable in a direction separating away from the inner needle.

3. The catheter assembly according to claim 2, wherein:
the elongated portion is engaged with the needle hub such that the elongated portion is movable relative to the needle hub, and
the needle hub inhibits the elongated portion from being curved when the elongated portion is engaged with the needle hub.

4. The catheter assembly according to claim 2, wherein the catheter is detachable from the holding portion by curving the elongated portion in a direction so as to separate the elongated portion away from the inner needle.

5. The catheter assembly according to claim 4, wherein the elongated portion holds the catheter with the holding portion by being housed in the needle hub in a manner formed in a linear shape in a width direction in front sectional view.

6. The catheter assembly according to claim 2, wherein the catheter is automatically detached from the holding portion when the elongated portion is curved in the direction separating away from the inner needle.

7. The catheter assembly according to claim 6, wherein the elongated portion is configured to hold the catheter with the holding portion by being housed in the needle hub in a manner formed in a bent shape in a width direction in a front sectional view, and the catheter is released from being held with the holding portion by forming the elongated portion in a linear shape in the width direction in the front sectional view, as the elongated portion is curved in a direction separating away from the inner needle.

8. The catheter assembly according to claim 7, wherein a bendable portion configured to induce the elongated portion to be formed in a bent shape in the width direction in the front sectional view is provided in a center portion of the elongated portion in a width direction.

9. The catheter assembly according to claim 1, wherein a plurality of the holding portions are provided in an axial direction of the catheter.

10. The catheter assembly according to claim 9, wherein the holding portions are formed in a manner such that the holding portions gradually become larger in a proximal end direction of the catheter operation member.

11. The catheter assembly according to claim 1, wherein the holding portion includes a pair of projecting portions configured to nip the catheter.

12. The catheter assembly according to claim 11, wherein the projecting portions of each pair of projecting portion are offset from one another in an axial direction of the catheter.

13. The catheter assembly according to claim 11, wherein:
the projecting portions of each pair of projecting portion include nail portions projecting in directions toward each other and configured to hook and hold the catheter, and
the nail portions include taper portions on a side opposite the holding section, the nail portions being inclined inward in a width direction.

14. The catheter assembly according to claim 1, wherein the catheter operation member includes a hub attachment portion attached to the catheter hub and configured to transmit operation force of a user to the catheter hub.

15. The catheter assembly according to claim 1, wherein the needle hub includes a guide portion configured to guide the catheter operation member in a direction separating away from the inner needle at the time of moving the catheter operation member in a distal end direction.

16. A method of using a catheter assembly, the method comprising:
providing a catheter assembly comprising:
a hollow catheter,
a catheter hub configured to fix and hold the catheter,
an inner needle including a needle tip and configured to be removably inserted through an inside of the catheter,
a needle hub configured to fix and hold the inner needle, and
a catheter operation member capable of moving the catheter relative to the inner needle,
wherein the catheter operation member includes a holding portion configured to directly hold the catheter in a detachable manner;
puncturing skin of an individual with the inner needle and the catheter while the needle is located inside the catheter and the holding portion directly holds the catheter;
advancing the catheter relative to the inner needle so as to insert the catheter into a blood vessel of the individual, by sliding the catheter operation member in a distal end direction relative to the needle hub while the holding portion directly holds the catheter;
retracting the inner needle and the needle hub; and
separating the catheter operation member from the catheter and the catheter hub.

17. The method according to claim 16, wherein:
the catheter operation member extends in a longitudinal direction of the needle hub and includes an elongated portion that includes the holding portion, and
the elongated portion is curvable in a direction away from the inner needle so as to separate from the inner needle.

18. The method according to claim 17, wherein:
the elongated portion is engaged with the needle hub such that the elongated portion is movable relative to the needle hub, and
the needle hub inhibits the elongated portion from being curved when the elongated portion is engaged with the needle hub.

19. The method according to claim 17, wherein the elongated portion holds the catheter with the holding portion by being housed in the needle hub in a manner formed in a linear shape in a width direction in front sectional view.

20. The method according to claim 17, wherein, during the step of advancing the catheter relative to the inner needle, when a distal end portion of the catheter operation member contacts the skin of the individual, the distal end portion of catheter operation member curves in a direction away from the inner needle and separates from the inner needle.

* * * * *